United States Patent [19]

Mandler et al.

[11] Patent Number: 5,474,184
[45] Date of Patent: Dec. 12, 1995

[54] PROCESS FOR PRODUCING DETERGENT AND THE LIKE IN REUSABLE AND RECYCLABLE RECEPTACLES, RECYCLABLE AND REUSABLE RECEPTACLES AND APPARATUS FOR USE OF FILLED RECEPTACLES

[75] Inventors: Gunter Mandler, Heuchelheim; Wolfram Rieber, Neuhofen; Richard Sander, Pfinztal-Berghausen; Jürgen Kompan, Römerberg, all of Germany

[73] Assignee: Ecosan Hygiene GmbH., Hanau, Germany

[21] Appl. No.: 324,909

[22] Filed: Oct. 18, 1994

Related U.S. Application Data

[63] Continuation of Ser. No. 17,877, Feb. 16, 1993, abandoned.

[30] Foreign Application Priority Data

Feb. 14, 1992 [DE] Germany .................... 42 04 489.8

[51] Int. Cl.⁶ .................................................. B65D 21/04
[52] U.S. Cl. .......................... 206/519; 206/508; 206/509; 220/770; 220/771; 215/398
[58] Field of Search ........................... 206/519, 515, 206/508, 509; 220/770, 761, 771, 23.83, 23.86, 254; 215/100 A, 399, 398, 396

[56] References Cited

U.S. PATENT DOCUMENTS

| D. 288,293 | 2/1987 | Arvans | D9/370 |
|---|---|---|---|
| 2,164,092 | 3/1958 | Smith | 23/107 |
| 2,842,277 | 7/1958 | Jewell | 215/100 A |
| 2,879,917 | 3/1959 | Flack . | |
| 2,920,417 | 1/1960 | Wertheimer | 45/28 |
| 3,581,928 | 6/1971 | Amand | 215/100 A |
| 3,727,889 | 4/1973 | Nagel | 259/1 R |
| 3,854,582 | 12/1974 | Martinelli | 206/508 |
| 4,058,474 | 11/1977 | Keyes et al. | 252/160 |
| 4,219,436 | 8/1980 | Gromer et al. | 252/135 |
| 4,225,052 | 9/1980 | Tector et al. | 206/508 |
| 4,231,476 | 11/1980 | Compton et al. | 206/519 |
| 4,254,891 | 3/1981 | Jeppsson | 270/359 |
| 4,288,000 | 9/1981 | Luker et al. | 206/508 |

(List continued on next page.)

FOREIGN PATENT DOCUMENTS

| 0375022 | 11/1989 | European Pat. Off. ........ C11D 17/00 |
| WO92/12062 | 7/1992 | WIPO . |

OTHER PUBLICATIONS

Derwent Publications Ltd., London, GB; AN 89–224560 & JP, A, 1 161 100 (Lion Corp.) 23 Jun. 1989, Abstract.

Primary Examiner—Stephen J. Castellano
Attorney, Agent, or Firm—Hill, Steadman & Simpson

[57] ABSTRACT

A recyclable, reusable container includes a unitary molded thermoplastic container body having a closed bottom end, an opposed open top and a sidewall tapering upwardly and outwardly from the bottom end to the top end at a stacking angle of from about 2° to about 7°. The bottom includes an inwardly and upwardly directed dome-shaped region therein including a handle grip portion defined in an outwardly facing side of the dome-shaped region. The container body defines an open smoothly rounded container cavity without any undercut portions which is adapted to storably receive and completely discharge material contents placed therein for storage and dispensing. A stepped outward shoulder is provided adjacent the top end to define an outwardly stepped sidewall portion provided with external threads. An internally threaded cover member is releasably engageable over the top end of the container body to selectively close off the top opening of the container. The container bodies and cover members are configured so that they may be stacked in telescoping nested relationship in a manner providing a minimum of stack height for storage space saving advantages. The container and cover member are both molded from high grade thermoplastic molding materials adapted for reuse and recycling. The new and improved containers are specially suited for use in dispensing detergents and other cleaning agents employed in automated flush dispensing systems.

8 Claims, 25 Drawing Sheets

U.S. PATENT DOCUMENTS

| | | | |
|---|---|---|---|
| 4,569,780 | 2/1986 | Fernholz et al. | 252/90 |
| 4,572,384 | 2/1986 | Vesborg | 215/1 C |
| 4,680,134 | 7/1987 | Heile et al. | 252/160 |
| 4,690,305 | 9/1987 | Copeland | 222/52 |
| 4,725,376 | 2/1988 | Copeland | 252/90 |
| 4,808,236 | 2/1989 | Davis, Jr. | 134/25.2 |
| 4,828,112 | 5/1989 | Vollrath et al. | 206/519 |
| 4,999,124 | 3/1991 | Copeland | 252/90 |
| 5,080,819 | 1/1992 | Morganson et al. | 252/90 |
| 5,190,157 | 3/1993 | Przytulla | 206/519 |
| 5,211,289 | 5/1993 | Matthews | 220/254 |
| 5,269,438 | 12/1993 | Kelsey | 215/100 A |

PROCESS FOR PRODUCING DETERGENT AND THE LIKE IN REUSABLE AND RECYCLABLE RECEPTACLES, RECYCLABLE AND REUSABLE RECEPTACLES AND APPARATUS FOR USE OF FILLED RECEPTACLES

This is a continuation of application Ser. No. 08/017,877, filed Feb. 16, 1993 now abandoned.

BACKGROUND OF THE INVENTION

The present invention relates to a process or method for producing detergent, laundry products, cleaning and rinsing agents, disinfectants and/or preservatives and multiway, i.e., recyclable, reusable and returnable receptacles, particularly for carrying out the process or method of the invention. In particular, this invention concerns a process for the production of pressed, molded and at least partially porous detergent, laundry products, cleaning and rinsing agents, disinfectants and/or preservatives without using a preheated melt or solution, in which a prefabricated premix consisting of powdery and/or granular active substances is prepared with or without mixing the prefabricated mixture with a binder, is then filled into a suitably molded, returnable receptacle and compacted by pressure, so as to form a compact block solidified in the receptacle and having a powder structure.

The invention also relates to returnable receptacles for carrying out the process or method of the invention, i.e., recyclable, returnable receptacles, and which are open on the top as well as conically widening upwards, which can be used for containing liquids, solid or powdery detergents, laundry products, cleaning and rinsing agents, disinfectants and/or preservatives, and particularly for carrying out the above-mentioned process in association with dishwashing and laundry machines. In particular, this invention concerns reusable or recyclable, detergent, laundry product, cleaning and rinsing agent, disinfectant and/or preservative containing, returnable receptacles especially suitable for use in association with laundry machines, which are constructed in such a way that detergent, laundry product, cleaning and rinsing agent, disinfectant and/or preservative is dispensed from the receptacle when a flow of aqueous liquid is impinged or impinges upon a surface of the detergent, laundry product, cleaning and rinsing agent, disinfectant and/or preservative, which is exposed thereto. Finally, the invention relates to the use of these returnable receptacles. With respect to the receptacles, including the lids therefor, according to the invention, it is relevant that both the filled and closed receptacles as well as the empty receptacles and the lids are constructed so that they are stackable with each other.

DESCRIPTION OF THE PRIOR ART

In addition to liquid, pasty or powdery detergents or laundry products, in the past, molded, piece-like, solid detergent or laundry products, such as soap cakes, syndet cakes, i.e., synthetic detergent cakes, toilet cones or tablets, molded detergents or laundry products for dishwashing and laundry machines, etc., have been known and used for a long period of time.

A general list is found, e.g., in the publication by H. E. Tschakert, *Seifen, Öle, Fette, Wachse*, 98, 1972, 793–801, 845–849, and ibid. 99, 1973, 3–7.

While the production of such molded, piece-like detergent or laundry products has been accomplished by means of pressing and extrusion (into tablets, briquets and the like), production of such products has also been achieved by casting a solution or melt capable of solidifying into molds. As compared to pressing, this casting technique has the advantage that complicated and, e.g., irregular shaped products, can also be produced in a simple manner.

In this case, the solution or melt is frequently cast into the molds in its heated condition and solidified by cooling. Having solidified, the resultant shaped product can either be removed from the mold and supplied to the user in a separate package, or the container used as the mold can simultaneously serve as a package for the detergent or laundry product, and the product is supplied to the user in combination therewith. The detergent or laundry product amount required for the respective intended use is usually dissolved, when in use, out of the molded, piece-like detergent or laundry product accommodated in its case in each application by the interaction with appropriate solvents, usually water.

Examples of such product formulations and production processes are listed, e.g., in *Tenside* 8, 1991, 275; *Tenside* 11, 1974, 330; *Seifen, Öle, Fette, Wachse*, 96, No. 23, 1970, 823, as well as the previously referenced publication by H. E. Tschakert.

Likewise, there is disclosed in "*Jahrbuch für den Praktiker*", Verlag für Chem. Ind. Ziolkowski, Augsburg, 1972, page 194; 1973, page 229; 1974, page 110 and pages 132, 134, 135, 1975, pages 116, 117, 118, 1976, pages 116–120, which is well known to those of ordinary skill in this art, various formulation examples of detergent or laundry products in different shapes produced by casting a heated melt or solution into molds and allowing the melt or solution to solidify by cooling.

Recent patent literature has also disclosed processes for producing solid detergent or laundry product shapes by filling a heated melt or solution into molds and allowing it to solidify by cooling, e.g., as disclosed in European patent application 0 003 769. Other literature discloses pouring alkaline aqueous solutions into such molds, e.g. European patent application 0 307 587 and German patent applications DE 35, DE 35 19 354, DE 35 19 355, and DE 36 34 812.

All of these previously known production processes for solid detergent or laundry products are accompanied, among others, by the following manufacturing or qualitative drawbacks:

a) in the case of production by means of tabletting, briquetting, etc., only shaped products of very simple form can be produced and, in addition, very expensive installations are required for processing; and b) in the case of the production by casting a melt or heated solution into a mold, considerable energy is required for melting and holding the initial mixtures and, further, due to automatically prolonged holding at elevated temperature, thermally susceptible formulation constituents suffer from increased damage or a higher degree of decomposition, as compared to the case in which no or only very short heating times are involved. EP-A-0 242 966 describes the solidification of a granular detergent or laundry product mixture in a receptacle by pouring an aqueous solution heated to more than 66° C. and up to 83.5° C. into a mold already filled with granular or powdered detergent, without stirring taking place, to fill spaces in the granular or powdered detergent from top to bottom.

This procedure includes the drawback that the upper portion of the mixture in the receptacle solidifies too rapidly when the soaking liquid contacts the powder mixture for the first time, so that, particularly when fine particles are present, due to abrasion, the liquid does not penetrate or insufficiently penetrates the lower portions of the mixture, thus rendering the block formation incomplete.

As explained above, special receptacles are used as molds or packages for the detergents, laundry products, cleaning and rinsing agents, disinfectants and/or preservatives. However, in the U.S.A., Europe and in Germany there is a demand for reusable, i.e., refillable, receptacles whose production material can be recycled. In this connection, recycling is understood to mean grade-pure recycling, i.e., material such that it is possible to reproduce the original containers from the recycled materials.

Due to increasing amounts of waste there is an increased demand for packaging systems which occupy the least possible packaging volume while maximizing filling volume. Furthermore, there is a need for mono-packages or unitary packages, the residue from which can be emptied simply and reliably when filled with substances which may pose a safety hazard. In the case of chemical products such as cleaning and rinsing agents, it is desirable to fill the packages, i.e., containers, with concentrates instead of highly diluted mixtures. It is thus possible to reduce With such packages, by a factor of 2 to 5, the costs of packaging, cleaning and rinsing agents. Another reduction in resources required is possible by using returnable receptacles, i.e., due to refilling and grade-pure recycling, which permits further reduction in cost by factors of 5 to 10. Although all of the recited requirements are desirable, some important demands have to be complied with for such returnable receptacles in this product group:

1. complete and simplest possible emptying of the residue before returning the receptacles for the purpose of refilling (to result in problem-free transportation and contamination-free refilling);
2. construction of the product receptacles in such a way that the volume required for handling them is reduced (e.g., by stacking them into one another), by reduction of volume requirements by factors of about 2 to 5 when empty (transportation costs are calculated by volume);
3. safety for the users with respect to the dispensing systems, i.e., the dispensing system in connection with the product receptacles has to be designed in such a way that the users are protected from contact with the product;
4. stable, long-lasting design for the highest possible life, i.e., a great number of refillings. Inscription, if possible, impressed, milled or attached in any other indelible manner, so that safe, product-type sorting is possible prior to the refilling, without additional labeling; and
5. the same kind of material for both the receptacle and the closure or lid, ensuring a good, ecologically beneficial disposal possibility in the final disposal.

The materials usable for the receptacles as well as the receptacle lids may comprise all thermoplastics from which the described pack elements can be produced by means of appropriate known production processes (e.g., blow molding, but particularly, and especially preferably, injection molding).

One precondition is that in the described package design, the plastics used have sufficient dimensional stability, and are capable of withstanding occasional impact loads or compressive forces of the type such packages, are exposed to in transit and when being handled in routine use, are able to withstand temperatures of between about 0° C. and about 85° C. (during final rinse section) and are able to withstand UV radiation (caused by natural or artificial light). Another precondition is that the plastics used must be compatible with the chemicals contained as filling for the receptacles (particularly, with detergents, laundry products, cleaning, rinsing, washing agents, disinfectants, water treating agents), even at elevated temperatures of up to about 85° C., as well as for prolonged exposure times at those or ambient temperatures.

It is also desirable that the plastics used can be either recycled (plastic granulate recovery), or supplied for unproblematic, thermal utilization, i.e., combustion, upon expiration of their multiple-use period. For this reason, it is preferable to use halogen-free, particularly, chlorine-free, plastics.

Thus, polyethylene and polypropylene, particularly HD-polyethylene (high density polyethylene) or polypropylene, are especially preferred materials.

SUMMARY OF THE INVENTION

It is, therefore, one object of the present invention to provide a process for the production of pressed, molded and at least partially porous detergent, laundry products, cleaning and rinsing agents, disinfectants and/or preservative blocks without having to utilize a pressing step requiring application of high levels of force, and without having to melt or dissolve a raw material mixture or parts thereof by application of thermal energy prior to filling the mixture into a mold.

It is another object of the invention to provide such a process wherein the production is conducted to result in a compact block of material which exhibits a powdery structure, or which is at least partially porous.

It is yet another object of the invention to provide new recyclable, returnable receptacles which are open on the top and conically widen upwardly. As a result of the construction, it is possible to rinse out all parts of these receptacles in a simple and easy manner (manually or by means of machines) for example, dishwashing machines. These novel, returnable receptacles are to be used for liquids, solids or powdery detergents, laundry products, cleaning and rinsing agents, disinfectants and/or preservatives and particularly, for carrying out the above-mentioned process for producing detergent and the like.

It is still yet another object to provide a recyclable detergent, laundry product, cleaning and rinsing agent, disinfectant and/or preservative containing, returnable receptacle especially suited for use in association with dishwashing and laundry machines. The construction is such that the detergent, laundry product, cleaning and rinsing agent, disinfectant and/or preservative is dispensed from the receptacle when a flow of aqueous liquid is directed to impinge upon a surface of the detergent, laundry product, cleaning and rinsing agent, disinfectant and/or preservative, exposed thereto. Also, the receptacle is such that it should be possible to meter the detergent or laundry product contained in the receptacle through a dosing device which is constructed for receiving the receptacle therein such that, in operation, the agents in the receptacle are dissolved by the dosing device.

In accordance with the invention, there is provided a process for the production of pressed, molded and at least partially porous detergents, laundry products, cleaning and rinsing agents, disinfectants and/or preservatives, without the use of a preheated melt or solution. A premix consisting of powdery and/or granular active substances and excipients of suitable particle size is prepared, filled into a suitably shaped, returnable receptacle and is compacted therein by applying pressure so as to form a detergent, laundry product, cleaning and rinsing agent, disinfectant and/or preservative block solidified within the receptacle.

Another aspect of the invention is to provide a process for the production of pressed, molded and at least partially porous detergents, laundry products, washing agents, cleaning and rinsing agents, disinfectants and/or preservatives, without using a melt or solution which has been preheated to over about 66° C. to 83.5° C., wherein:

a) a prefabricated mixture consisting of powdery and/or granular, active substances and excipients of suitable particle size is produced in a suitable mixer, preferably a continuous mixer, optionally after mixing with a suitable, water-soluble or water-hydratable binder which is liquid or sufficiently flowable at its manufacturing temperature, to result in a moistened, yet still free-flowing powder composition;

b) the powder composition is filled into an appropriately shaped, returnable receptacle; and c) the composition is compacted by means of applying a pressure thereto of between $1 \times 10^4$ to $1 \times 10^6$ Pa, so as to form a detergent, laundry product, cleaning and rinsing agent, disinfectant and/or preservative block solidified in the receptacle.

In one aspect, the premixed composition is mixed with potentially thermally relatively unstable, active substances and additives. Such substances and additives can include but are not limited to active-chlorine, or active-oxygen substances, flavors or dyes, which are conventional and known to those of ordinary skill in this art.

In another aspect, the invention relates to a recyclable, returnable receptacle which is open on the top and conically widens upwardly toward its opening. A cover is attachable to the open top for sealing liquid, solid or powdery detergents, laundry products, cleaning and rinsing agents, disinfectants and/or preservatives therein, particularly for carrying out the process as outlined above. The filled and closed receptacle, the empty receptacle and the cover, each, per se, are stackable, and the stackable, dimensionally stable, returnable receptacle has a stacking inclination relative to a vertical axis thereof, and has an open, rounded shape without undercuts. The bottom of the receptacle includes a recess, optionally of dome shape, having a grip projecting from the bottom for transporting and/or handling the receptacle.

In yet still another aspect, the invention relates to a recyclable detergent, laundry product, cleaning and rinsing agent, disinfectant and/or preservative containing and returnable receptacle especially suitable for use in association with dishwashing and laundry machines. The receptacle is constructed in such a way that the detergent, laundry product, cleaning and rinsing agent, disinfectant and/or preservative is dispensed from the receptacle when a flow of aqueous solution is impinged or impinges upon a surface of the detergent, laundry product, cleaning and rinsing agent, disinfectant and/or preservative, exposed thereto. The receptacle is further characterized by having been filled with detergent, laundry product, cleaning and rinsing agent, disinfectant and/or preservative in the receptacle which was obtained according to the process described above.

In yet another aspect, the invention relates to the use of a returnable receptacle as described above for liquids, solid or powdery detergents, laundry products, cleaning and rinsing agents, disinfectants and/or preservatives.

In another aspect, the invention concerns the use of a returnable detergent, laundry product, cleaning and rinsing agent, disinfectant and/or preservative receptacle as described above for the purpose of washing, cleaning, rinsing and/or disinfecting and/or for the anti-microbial or deodorizing treatment of circulating water and/or water-supply systems.

The present invention is also directed to a device for dissolving detergents, laundry products, cleaning and rinsing agents, disinfectants and/or preservatives, which includes:

a) a tightly closable container having a dosing strainer resting upon a base thereof, the strainer being shaped to accommodate the substances to be dissolved which are disposed in the product receptacle;

b) a sprayer arranged concentrically below the strainer within a discharge for the receptacle; and c) a discharge nozzle arranged concentrically within the discharge.

The device includes a product receptacle as outlined above which is placed on the dosing strainer.

It has been unexpectedly discovered that a solidified, compacted, but not fusion-cast detergent, laundry product, cleaning and rinsing agent, disinfectant and/or preservative block, which still exhibits a powder structure, can be produced by mixing a prefabricated premix consisting of powdery and/or granular active substances and excipients, with a suitable, water-soluble binder, preferably liquid binder, at the production temperature in an appropriate mixer, preferably a continuous mixer, so that a moistened, yet still free-flowing powder composition results. This powder composition, which can also be worked optionally without initial binder addition, is compacted by applying pressure, without pressing too strongly, so that a compact block forms in the subsequent solidification, which still exhibits a powder structure. The above-mentioned binder addition step is not necessary in all cases, because the active substances used for some compositions contain water of crystallization, which may be sufficient to create a moistened, yet still free-flowing powder composition.

When a binder is used, it typically makes up with the composition a moiety with a mixture of about 1% to about 29% based on the total weight of the composition including the binder. The binder is typically water, an aqueous solution, a dispersion of one or more water-soluble salts, an organic substance, a heated flowable melt or a gel. The binder can but need not be crystallizable at about 0° C. to about 40° C. In one embodiment the binder contains components having cleaning activity, i.e., are capable of being used for cleaning. The components for the binder can comprise an aqueous 30% to 60% solution, by weight, of alkali-(ortho, pyro or poly)phosphates.

Having generally described the invention, the same will become better understood from the following detailed description made with reference to the attached drawings.

Figure 1:
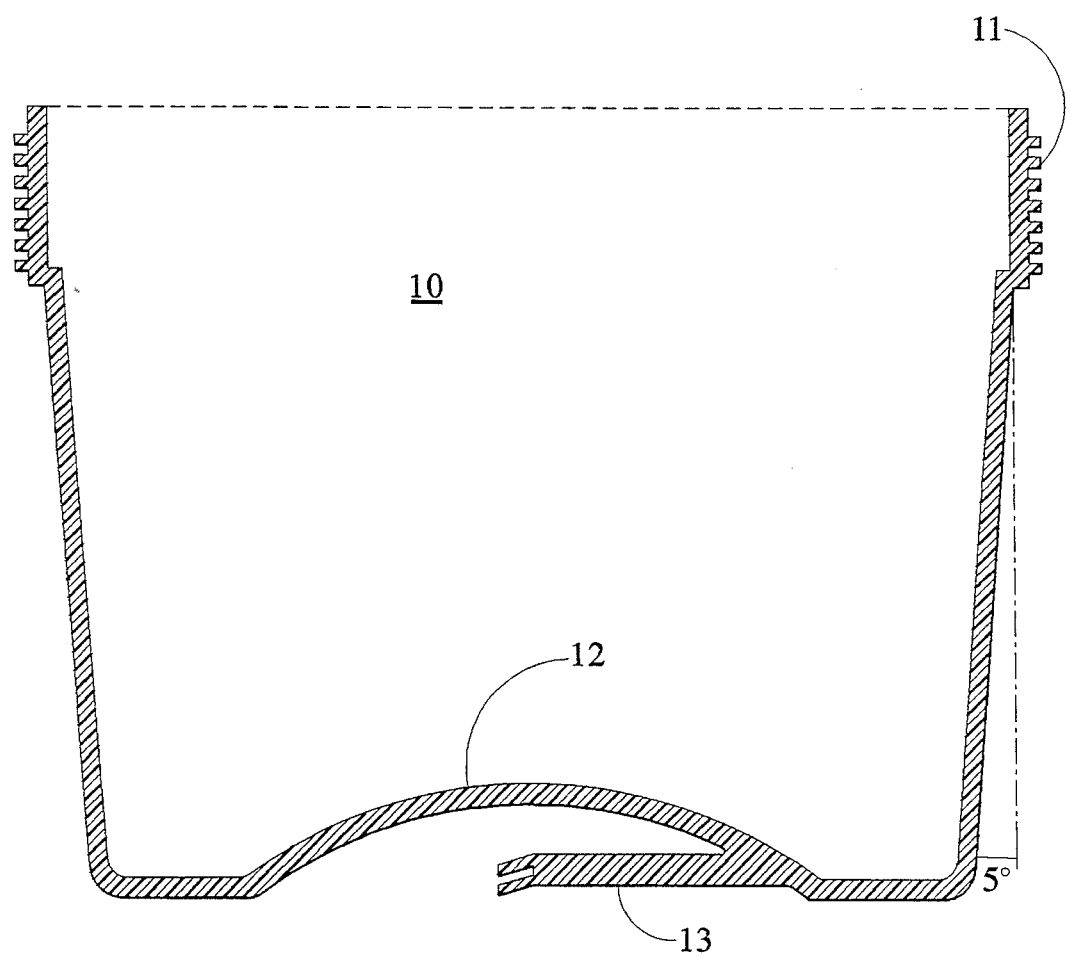
FIG. 1 is a cross-sectional view through an empty product receptacle according to the invention made of, e.g., 2 mm thick high density, i.e., (HD), polyethylene, which is produced as an injection molded article which can be filled with powder granulate.
Figure 2:
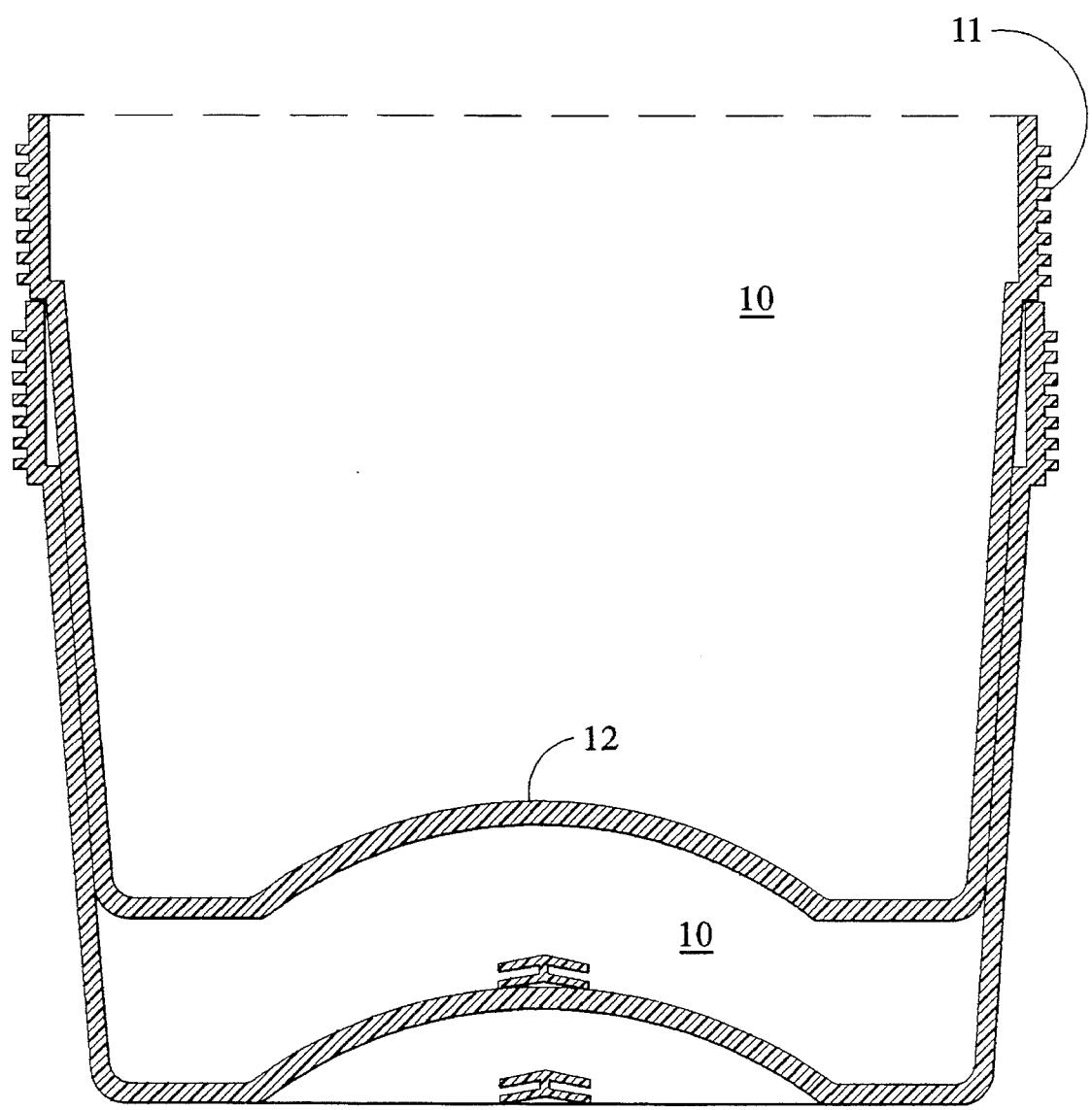
FIG. 2 is a cross-sectional view of two receptacles according to the invention stacked on each other.

DETAILED DESCRIPTION OF THE PREFERRED EMBODIMENTS.

The recyclable receptacles 10, 20, 30, 40 and 60 in accordance with the invention are illustrated in FIGS. 1–5, FIGS. 8–9, FIGS. 16–19 and FIGS. 22–25. The receptacles 10, 20, 30, 40 and 60 are open on the top and widen conically upwards. They are shaped so as to be capable of containing liquids, solid or powdery detergents, laundry products, cleaning and rinsing agents, disinfectants and/or preservatives. The receptacles 10, 20, 30, 40 and 60 are typically made of a 2 mm thick, high density polyethylene, made by an injection molding technique which is conventional and well known to those of ordinary skill in the art. Preferably, to allow stacking, the receptacles 10, 20, 30, 40 and 60 are inclined along the side wall thereof, i.e., have a stacking inclination, at preferably about 5° from their vertical axis of the receptacles as shown in FIGS. 1, 3, 4, 5 and 8. A broader range of stacking inclination can be employed, depending on volume, as is discussed hereinafter. The receptacles are completely open i.e., continuous, towards the filling and dosing opening without any cuts in the walls or obstructions, i.e., undercuts.

As shown in FIGS. 1–5, 8 and 9, on the open side of each receptacle 18, 20, 30, 40 and 60 there is external thread 11, 24, 34, 44 and 63 which serves for having the solid screw-on lid 50, 70, 90 and 100 of FIGS. 6, 7, 10, 11, 14a, 14b and 15 secured to the top of the receptacles 10, 20, 30, 40 and 60, for sealing the contents thereof. The lid 100 of FIG. 15, the lids 110, 130 and the product receptacle bottoms 12, 23, 42 and 61 of FIGS. 1–5, 8 and 9 each include respective handles 13, 22, 33, 43, 62 and 101 so that the product receptacles 10, 20, 30, 40 and 60 can easily be handled, transported and opened. The solid closures 50, 70, 90, 100 serve to seal the receptacles 10, 20, 30, 40 and 60 to provide safe storage and transportation.

Figure 10:
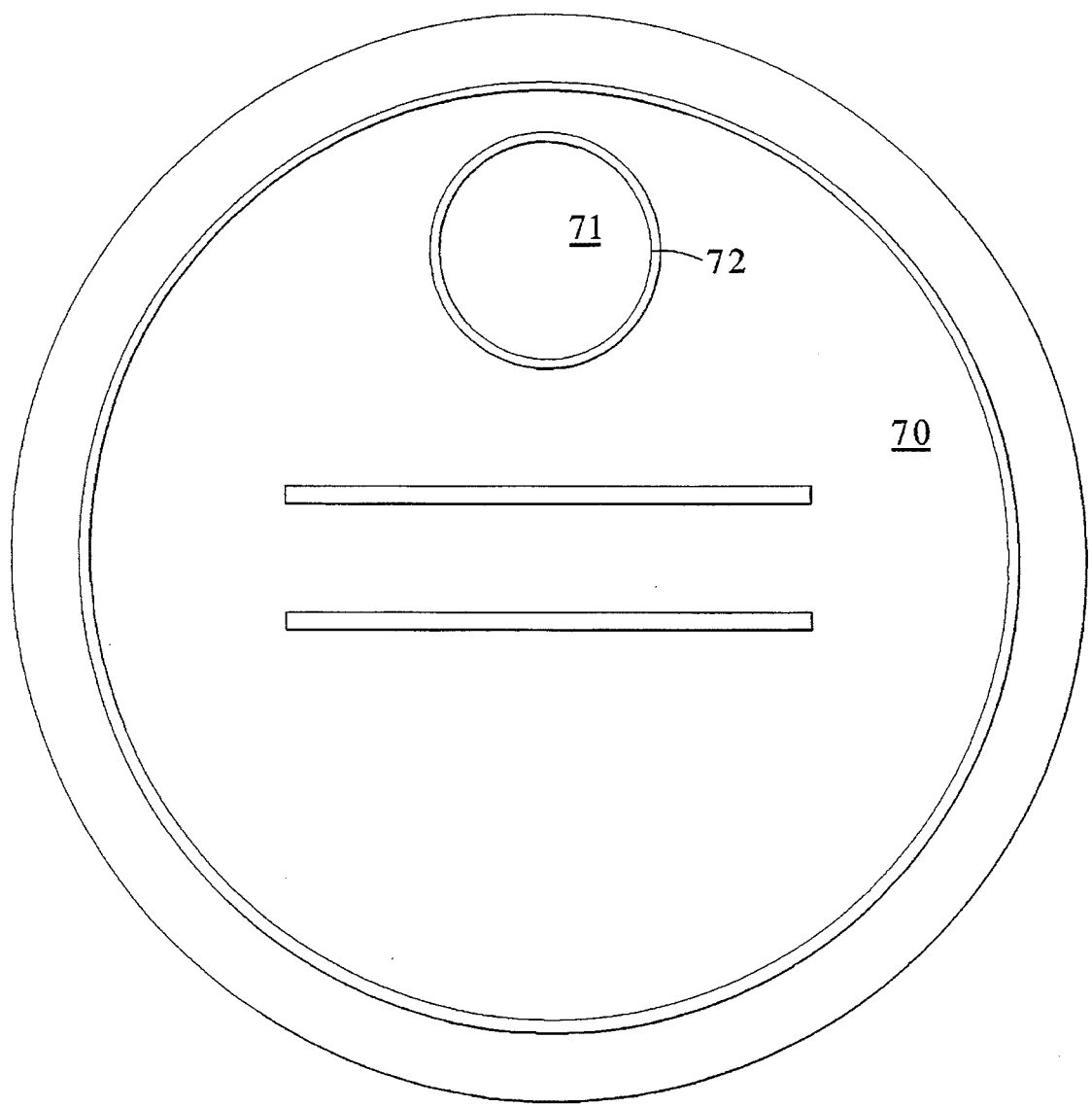
FIG. 10 is a top view of a special embodiment of the lid according to the invention which has its own smaller lid or opening, including a receiving thread therefor.

In one embodiment of the lids 50, 70, 90, 100, 110, 130 a smaller lid mounted on the larger lid for the receptacle as shown, for example, by lid 71 of FIG. 10. However, in most cases it is not necessary to provide such smaller lids. In another embodiment of the invention (c.f.s. FIG. 16 to 25) the lids 113,130 have sealings 120 consisting of usual materials for sealings. The lids 100, 130 comprise also a handle 116.

Figure 4:
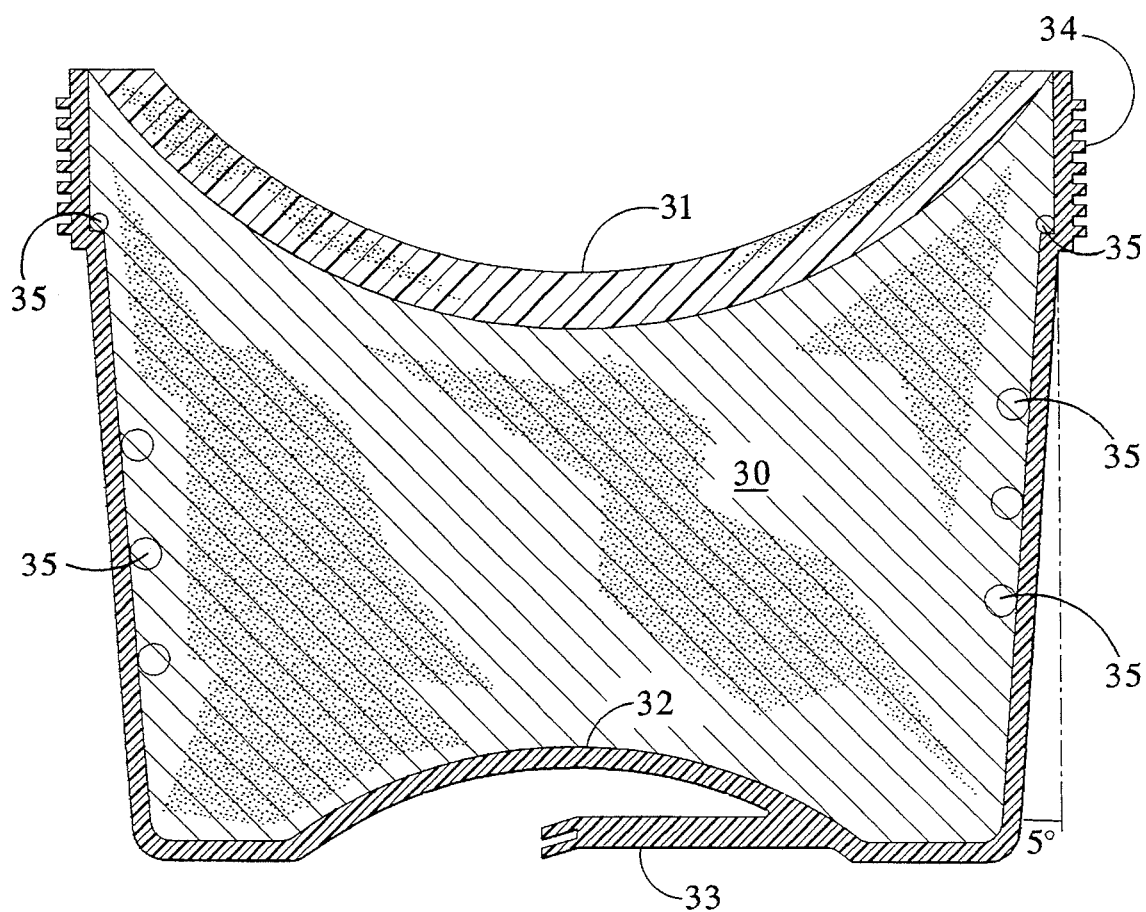
FIG. 4 is a cross-sectional view of a receptacle according to the invention, which is filled to the top with detergent, laundry product, cleaning and rinsing agent, disinfectant and/or preservative (with or without the addition of binder) and onto which a retaining layer has been fused.

In another embodiment, one or more retaining members 35 can be mounted on the inner side of the receptacle wall as shown in FIG. 4. The retaining members 35 serve to help hold the contents of the receptacles 10, 20, 30, 40 and 50 "in mass" therein.

In the case where liquid fillings are used in place of solid or granular fillings, they can be poured out of the receptacles according to the invention in required quantity, e.g., by means of outlet aids or cocks, or they can be sucked out of the packs or dosed by means of pumps and suction lances providing dosage control. Such devices are conventional and well known to those of ordinary skill in the art.

Figure 11:
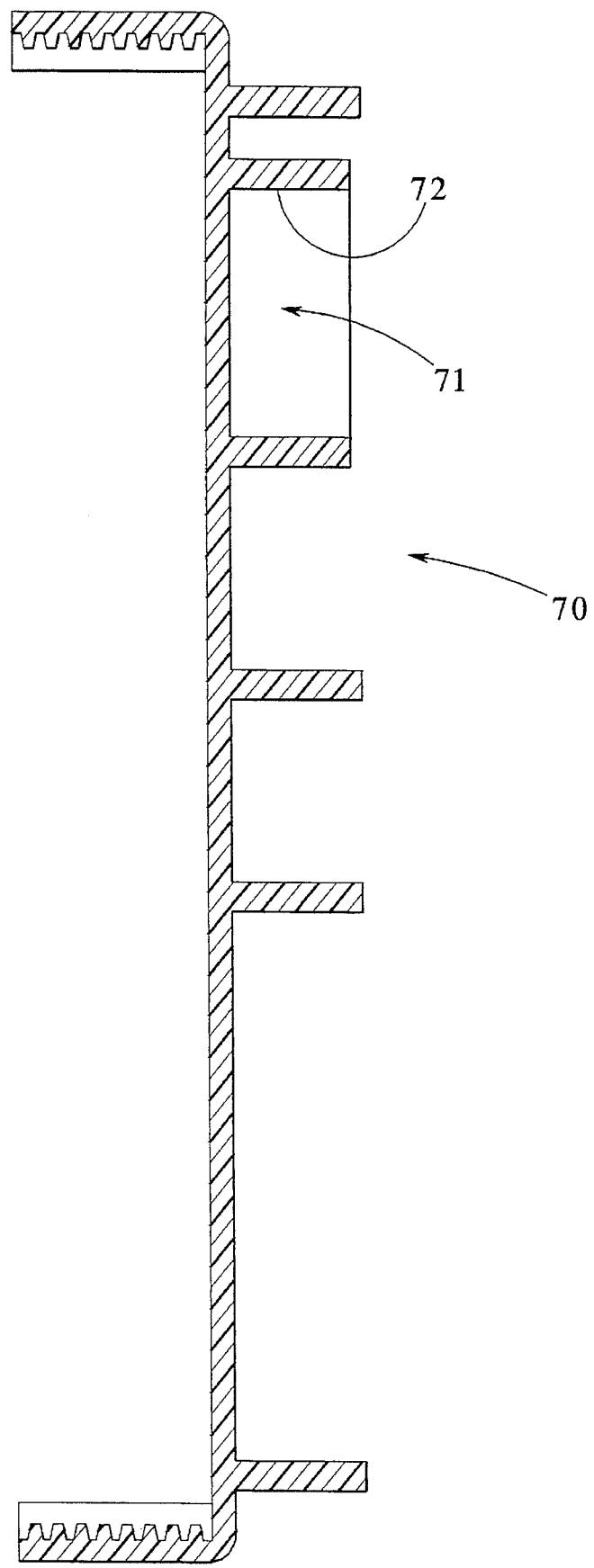
FIG. 11 is a side, cross-sectional view through the lid of FIG. 10.

In one embodiment, a small lid 71 fixed to the larger lid 70, as shown in FIGS. 10 and 11, is opened and commercially available suction lance for a suction jet device may be inserted. The dosage, i.e., the suction out, is continued until the product receptacle is completely empty. The large screw-on lid 70 can then be screwed off. The suction lance can then be taken out and then inserted into a new receptacle filled with the product which has had lid 70 with small lid 71 placed thereon. Alternatively, the small lid 71 can be a degassing valve for allowing gases in the receptacle to be released therefrom. The lid 70 can also include associated therewith a flat seal such as a sheet covering the opening of the receptacle under the lid 70. Alternatively, the seal can be an O-ring which seals around the edge of the open end of the receptacle with the lid 70.

Figure 12:
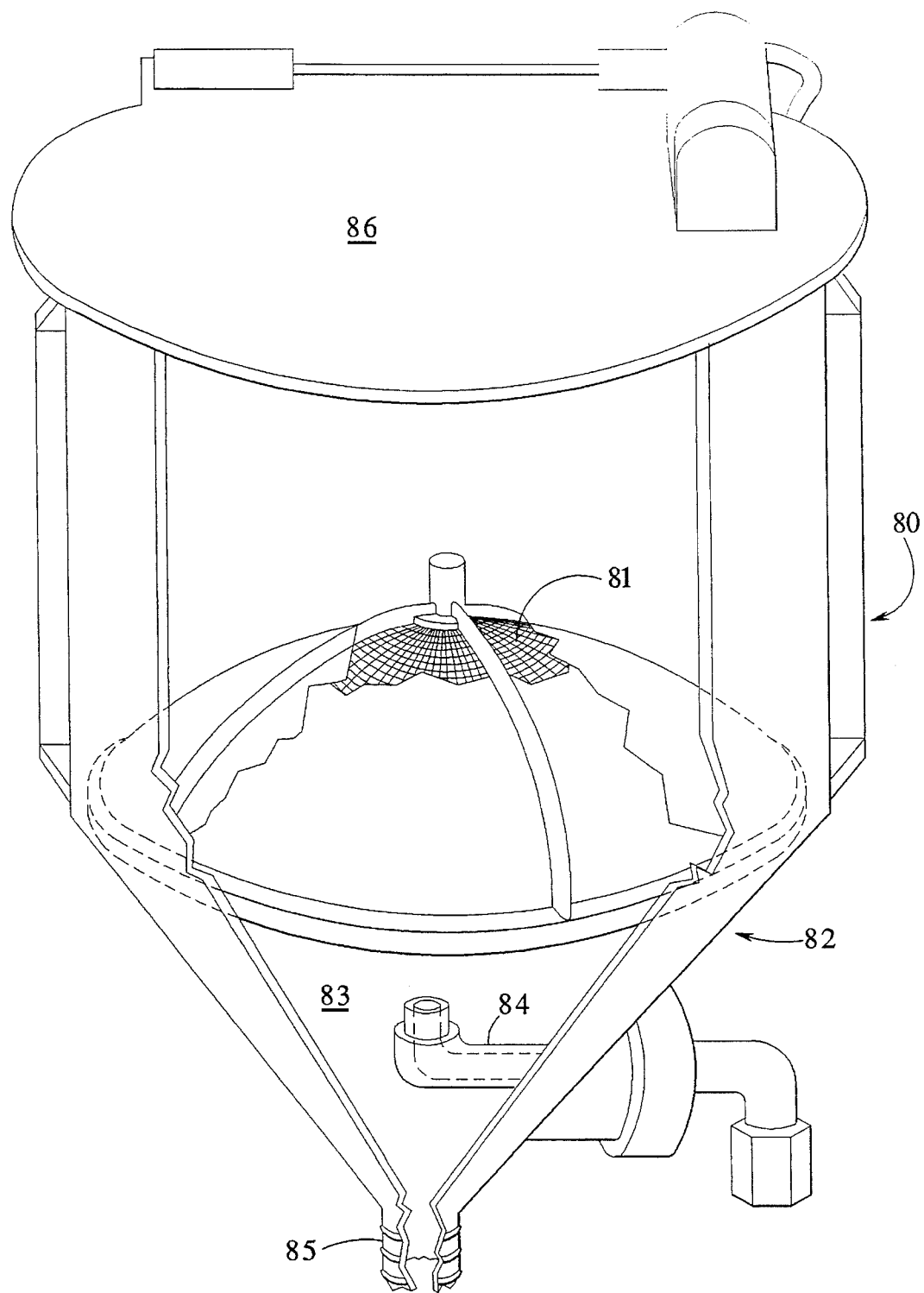
FIG. 12 is a partly cut-away, perspective view of a dosing device for dissolving detergents, laundry products, cleaning and rinsing agents, disinfectants and/or preservatives.
Figure 13:
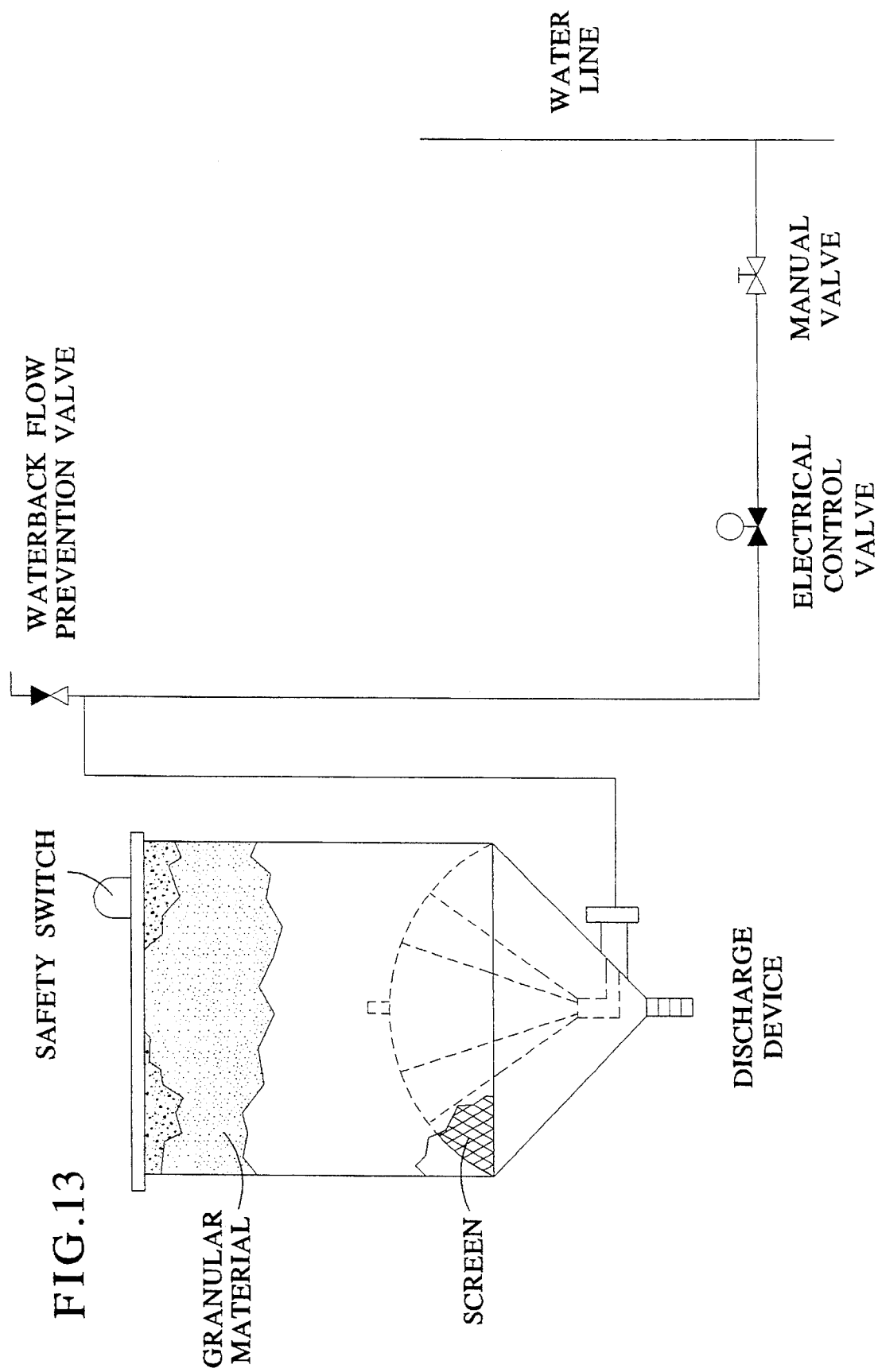
FIG. 13 is a schematic diagram of the dosing device of FIG. 12, shown connected to a water-supply line through an arrangement of valves.
Figure 14A:
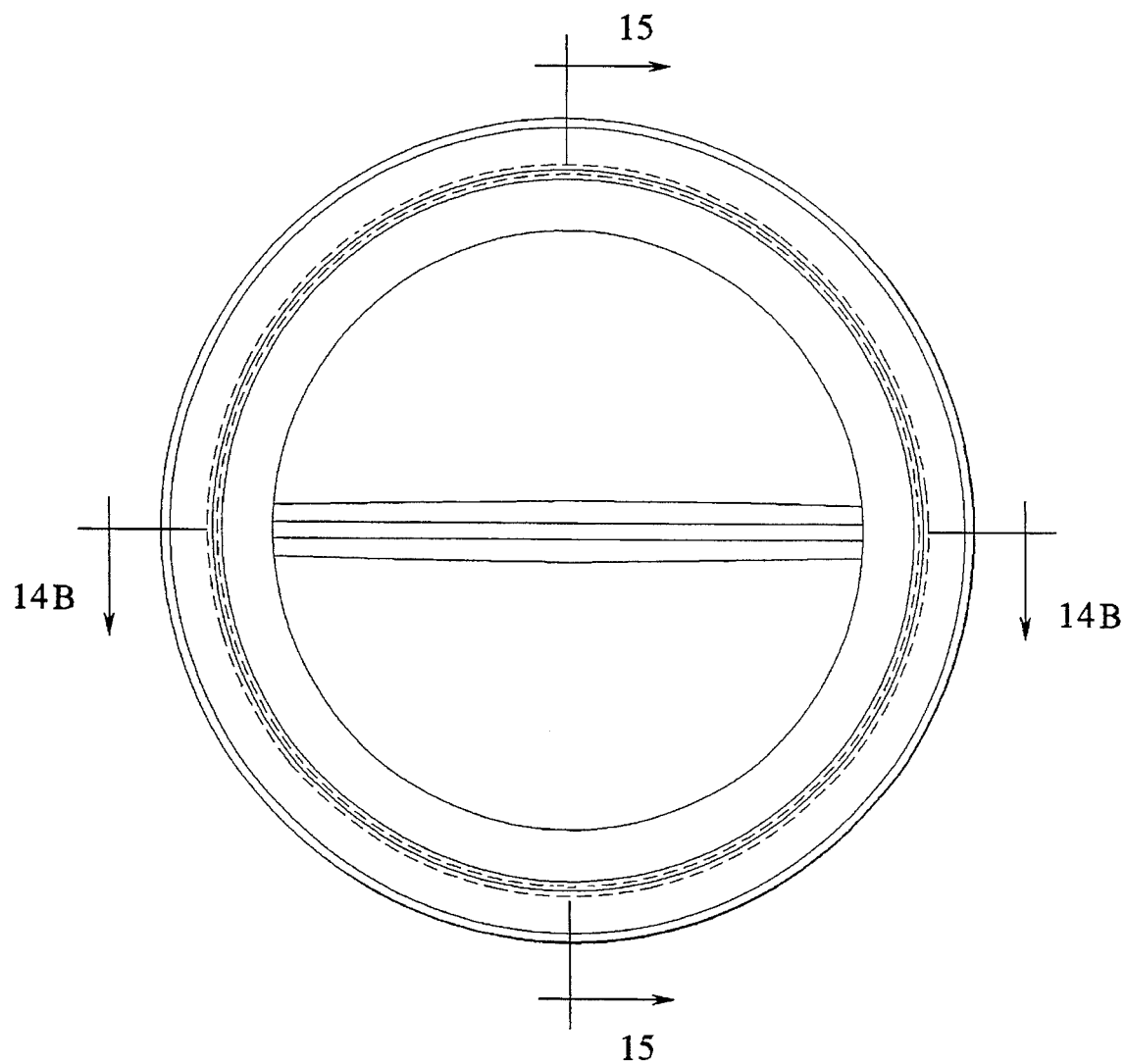
FIGS. 14a and 14b are a top and side, cross-sectional view, respectively, of an alternative embodiment of a recessed lid which may optionally be dome-shaped for use with the receptacle of the invention.
Figure 14B:
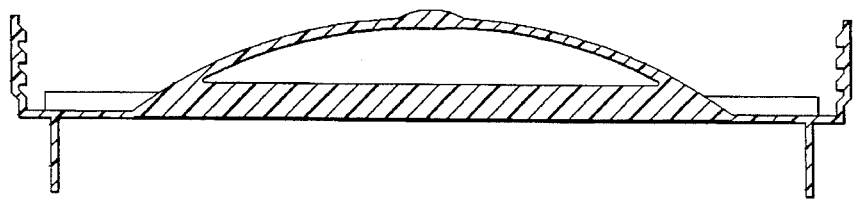
Figure 15:
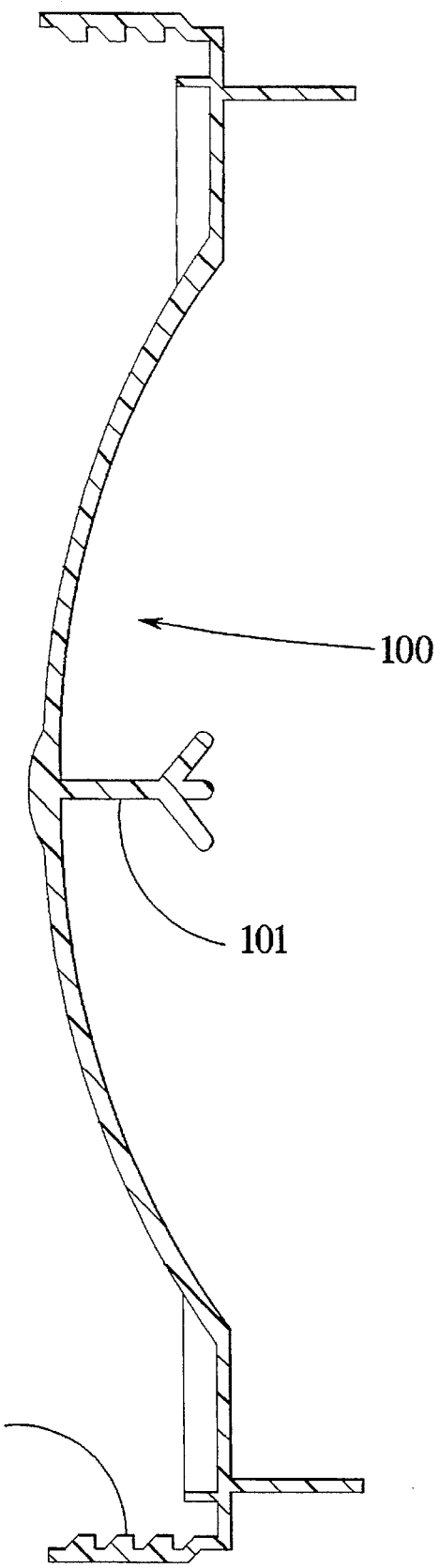
FIG. 15 is a cross sectional view of another embodiment of a recessed, dome-shaped lid having a grip extending from the top thereof.
Figure 16:
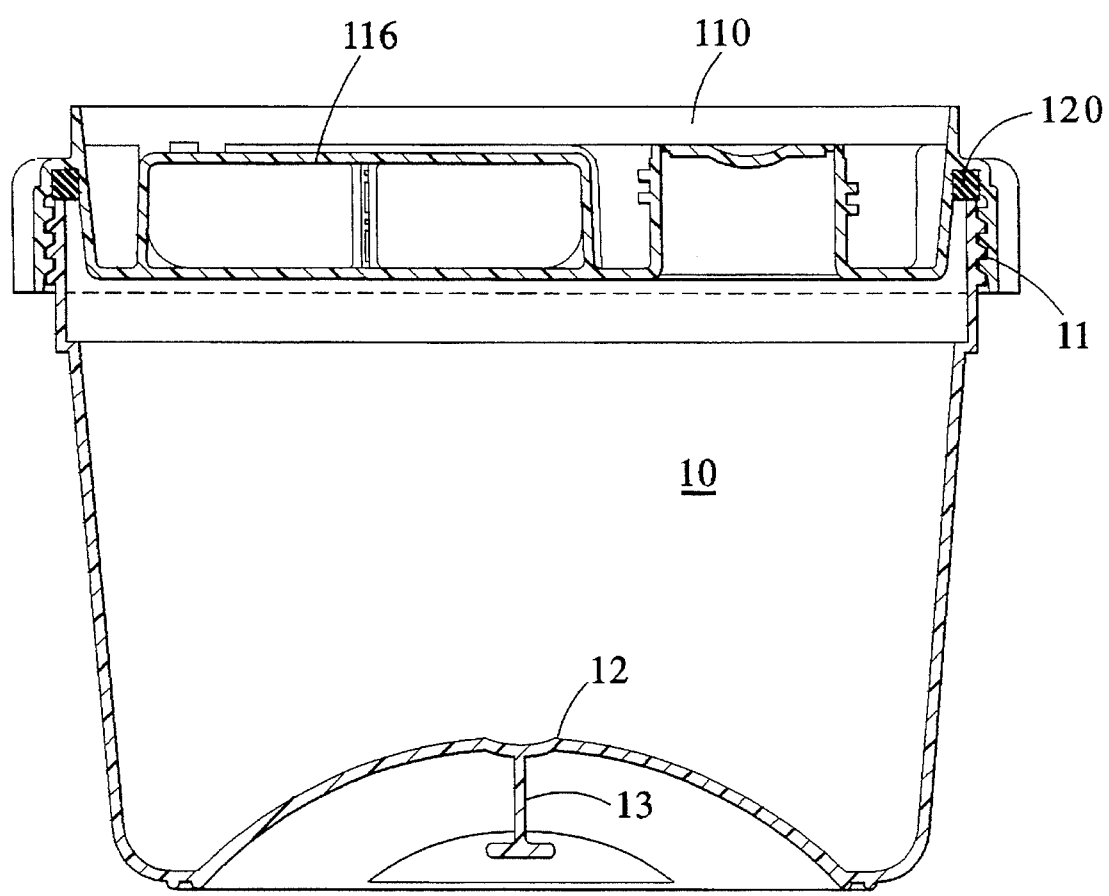
FIG. 16 is a cross-sectional view through an empty product receptacle of another embodiment of the invention showing a 2.5 kg receptacle.
Figure 17:
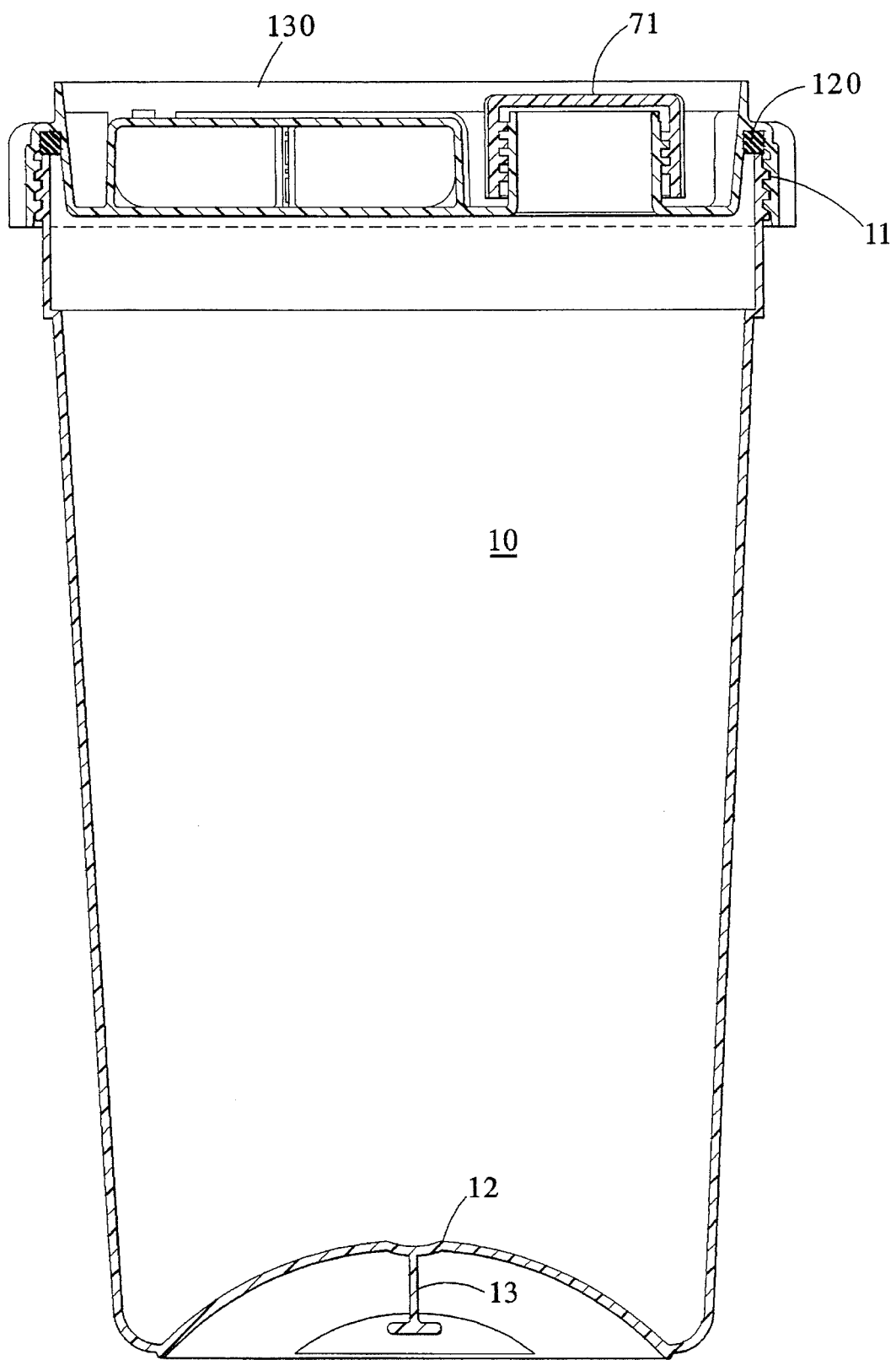
FIG. 17 is a cross-sectional view through an empty 1.5 l receptacle according to another embodiment of the invention including a small lid.
Figure 18:
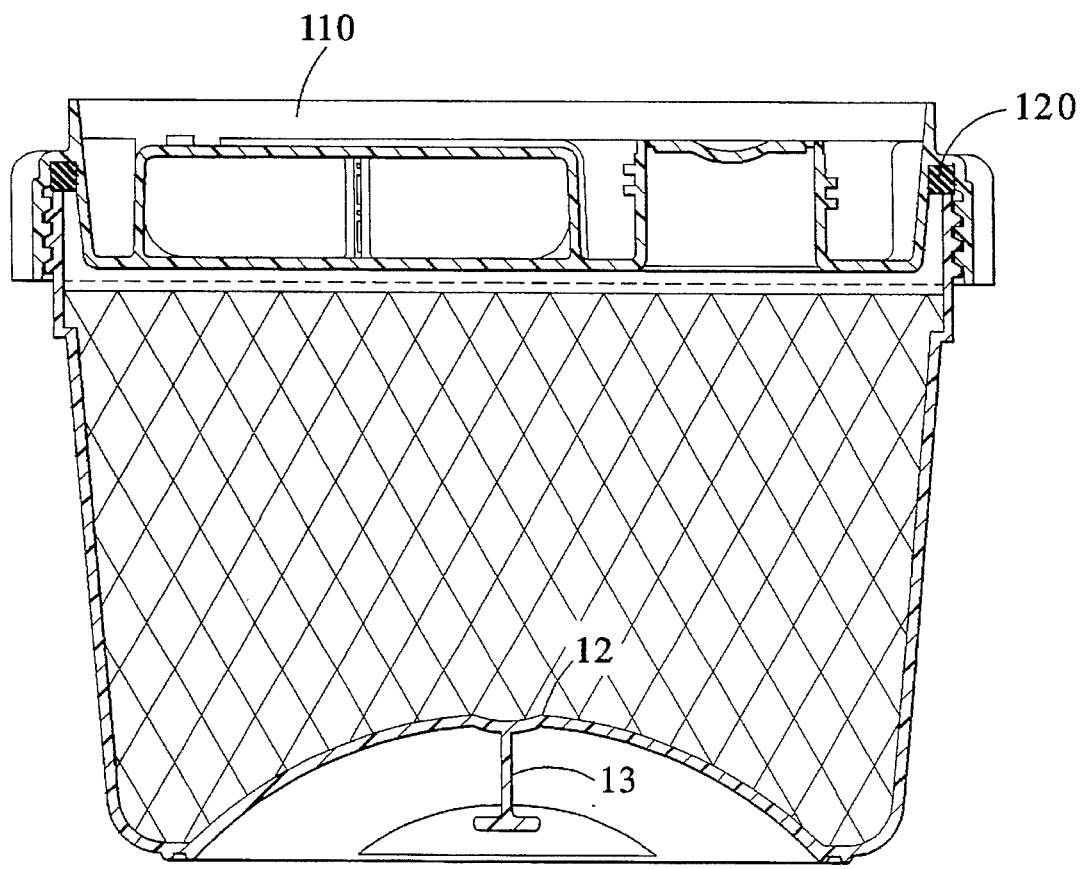
FIG. 18 is a cross-sectional view of a 2.5 kg receptacle according to the invention filled to the top including a lid.
Figure 19:
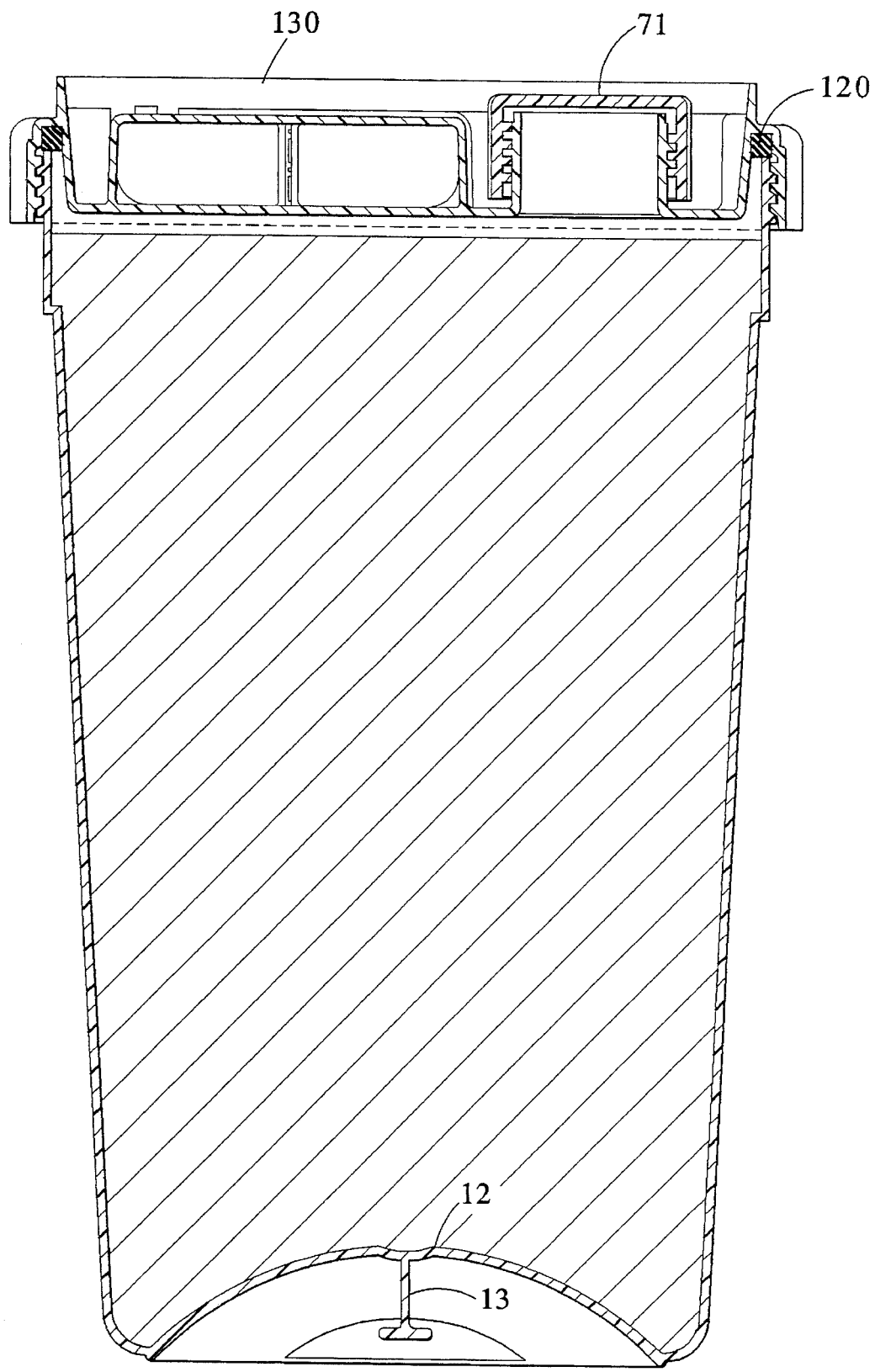
FIG. 19 is a cross-sectional view of the 5 l receptacle according to the invention, filled to the top with detergents, laundry products, cleaning and rinsing agents, disinfectants and/or preservatives, including a big and small lid.
Figure 20A:
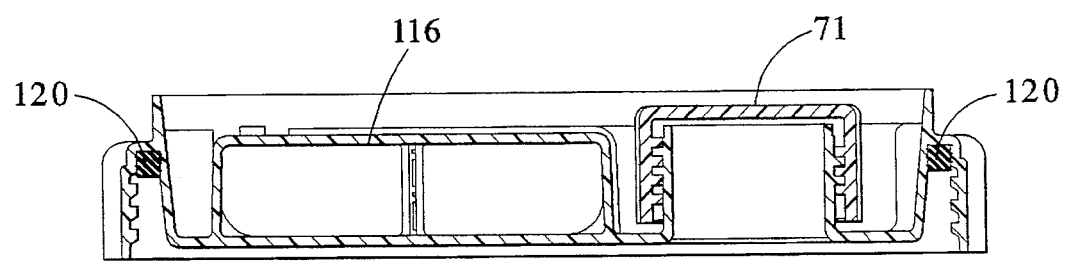
FIGS. 20(a) and 20(b) are cross-sectional views of special embodiments of the lids according to the invention showing an open version of a smaller opening closed by lid 71 in FIG. 20(a), and in FIG. 20(b) showing the smaller opening not closed by a lid 71, but closed by a synthetic resin, i.e., molded over with or by a polymer or polymeric material.
Figure 20B:
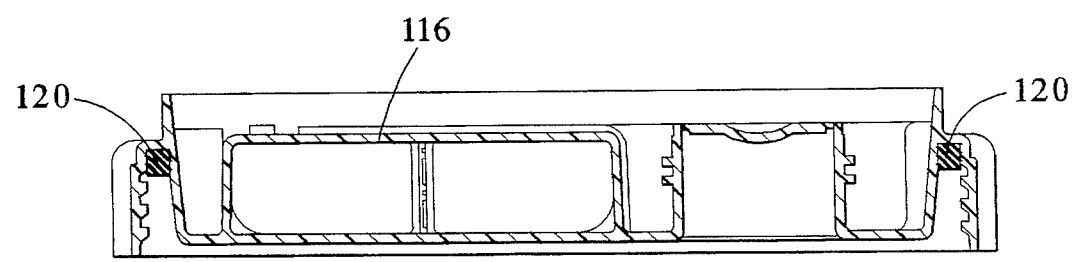
Figure 21:
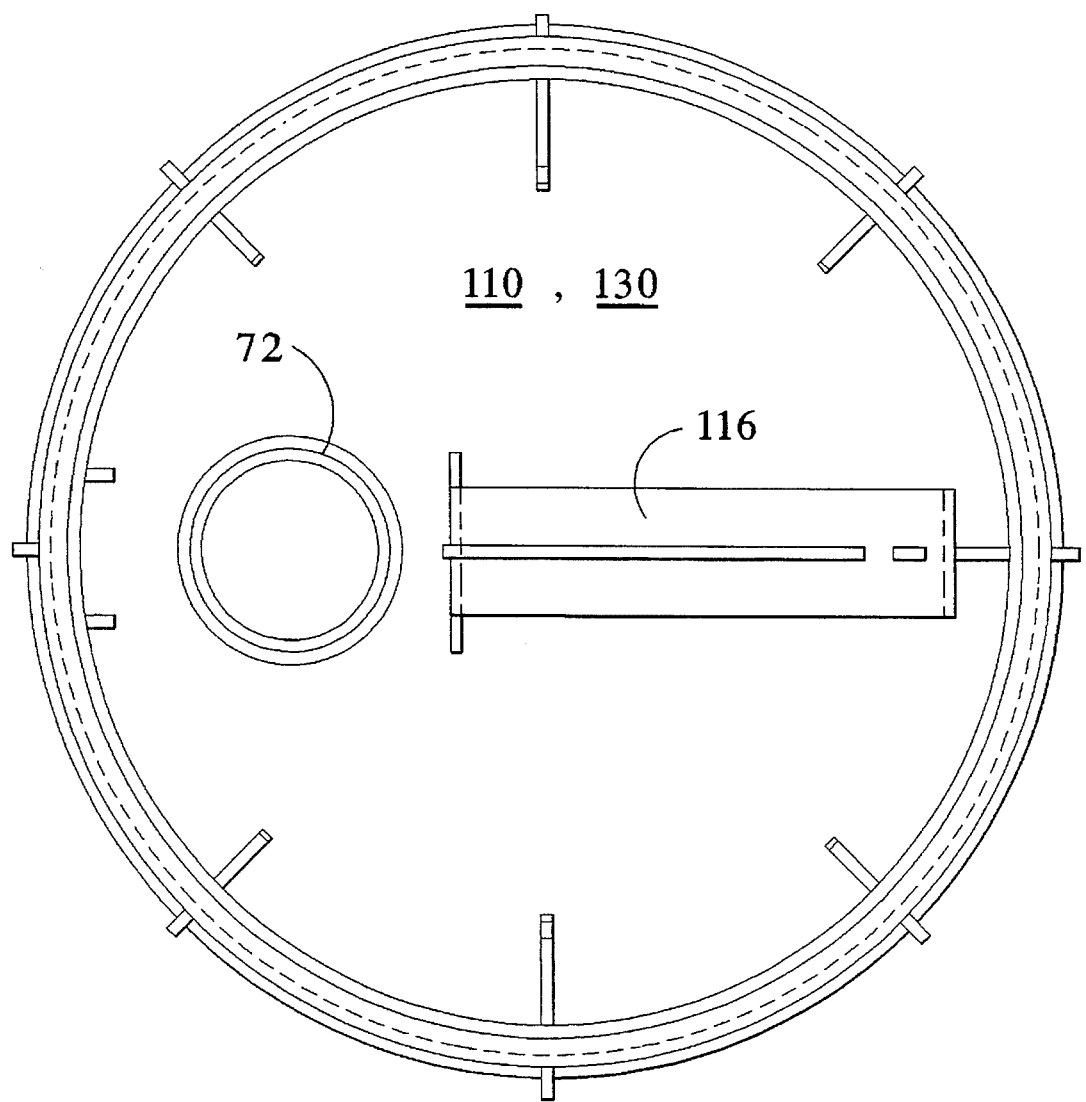
FIG. 21 is a top view of a special embodiment of the lid according to the invention which has its own smaller lid or opening including a receiving thread therefor and a handle
Figure 22:
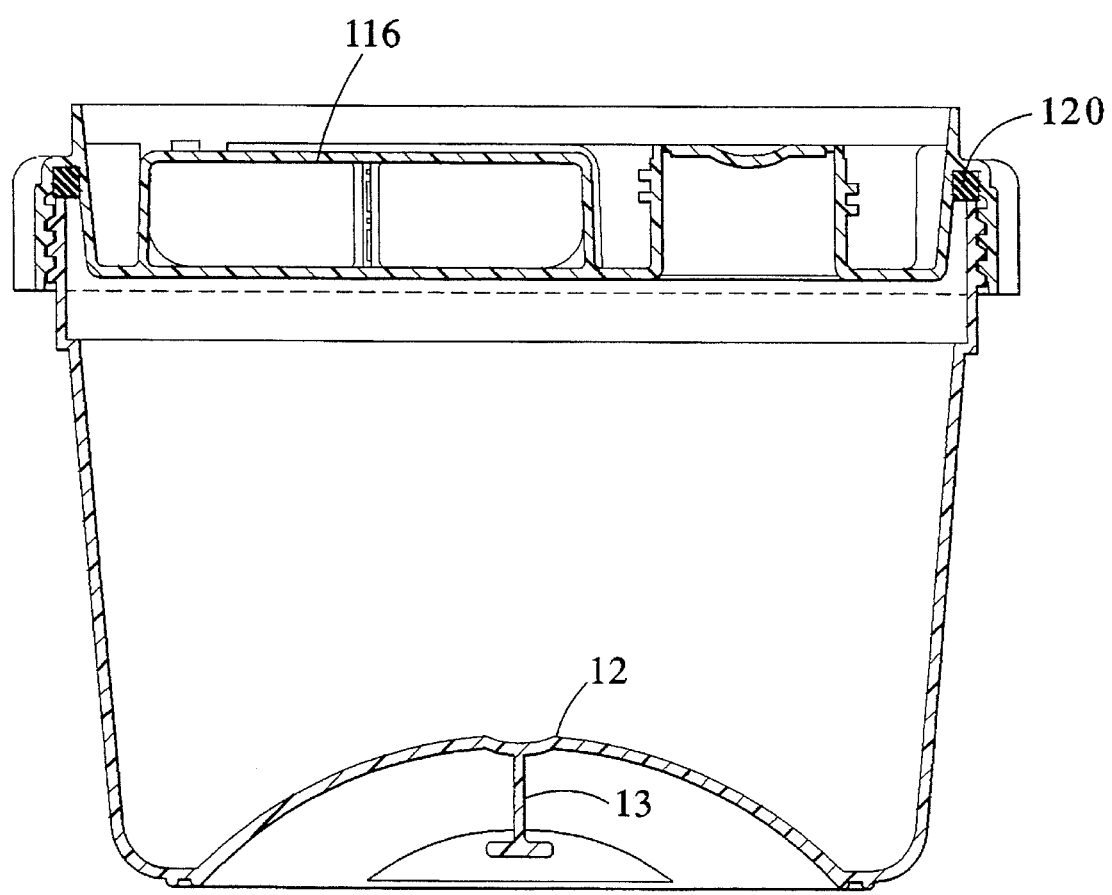
FIG. 22 is a cross-sectional view of a 2.5 kg receptacle according to the invention including a seal 120.
Figure 23:
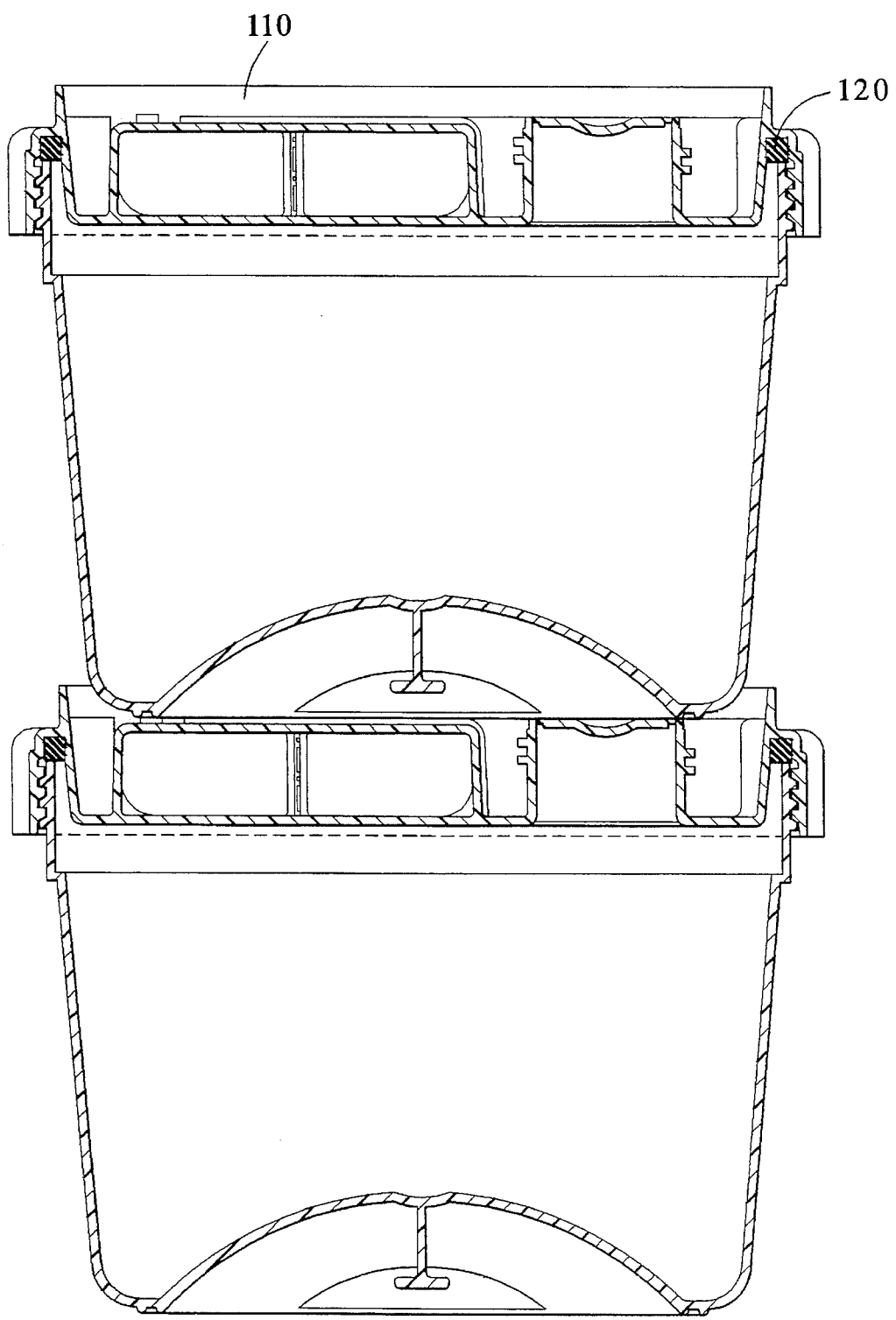
FIG. 23 is a cross-sectional view of two receptacles of 2.5 kg according to the invention, filled to the top thereof, and stacked on each other, with lids and seals thereon.
Figure 24:
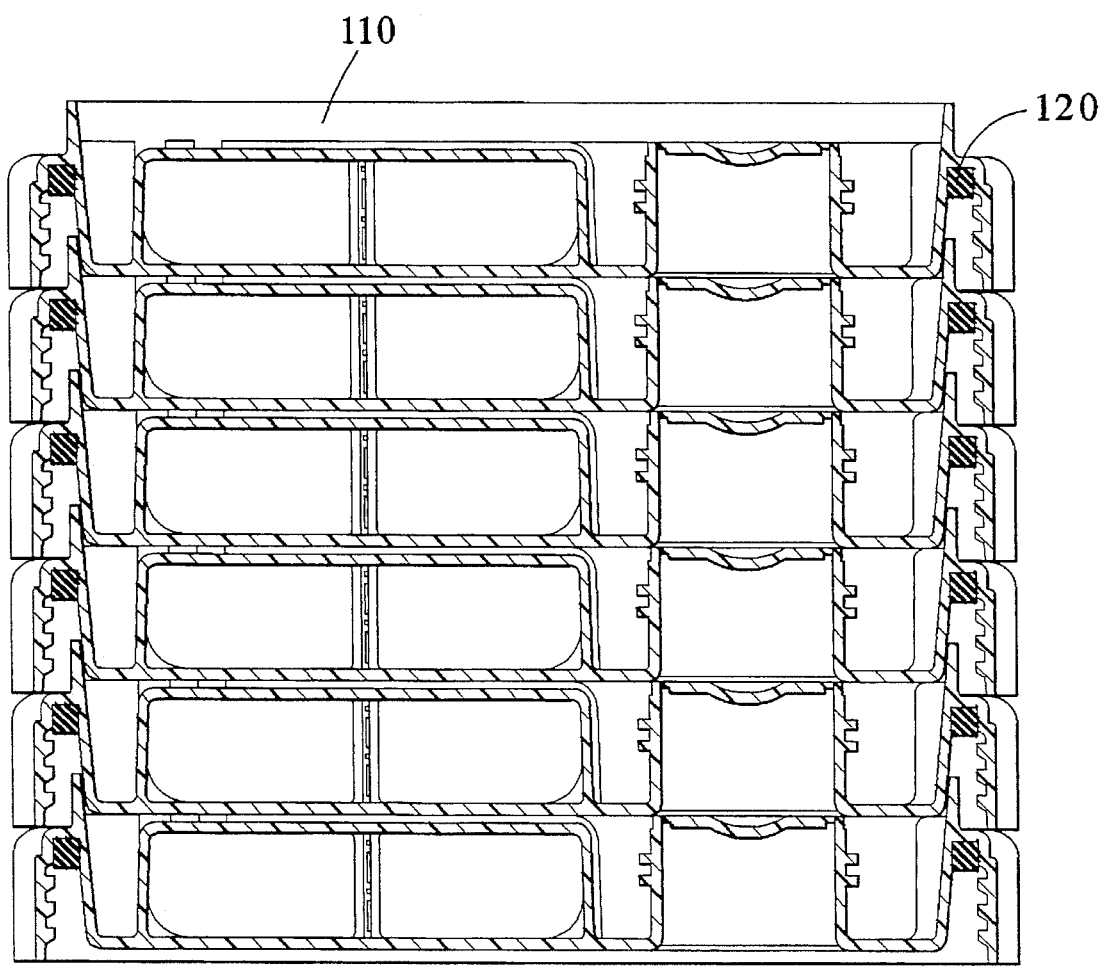
FIG. 24 is a cross-sectional view of several lids, including seals, stacked on each other.
Figure 25:
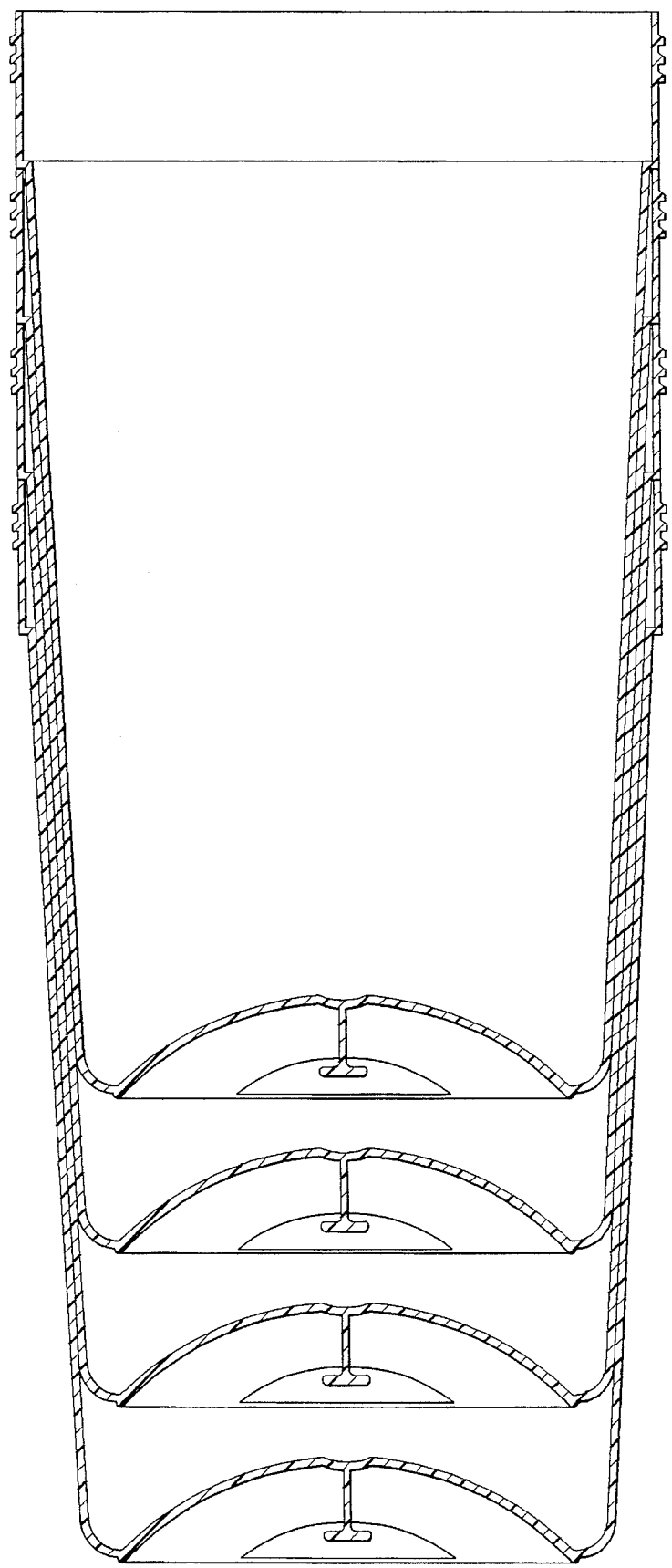
FIG. 25 is a cross-sectional view of four, 5 l receptacles, in empty condition, according to the invention shown stacked on each other.

Powdery and granular fillings can be removed from the receptacle according to the invention either as usual or, if during the filling, the surface was sealed in a suitable manner against flowing-out, be dissolved and discharged by placing the receptacle with its opening facing downwards into a dosing device 80 equipped with a strainer 81 which device 80 impinges a controlled, pulsating spray upon the granulate surface 82. In this manner the fillings can be supplied in precise doses to the system. Such an arrangement is shown in FIGS. 12 and 13 to be discussed hereinafter.

Figure 3:
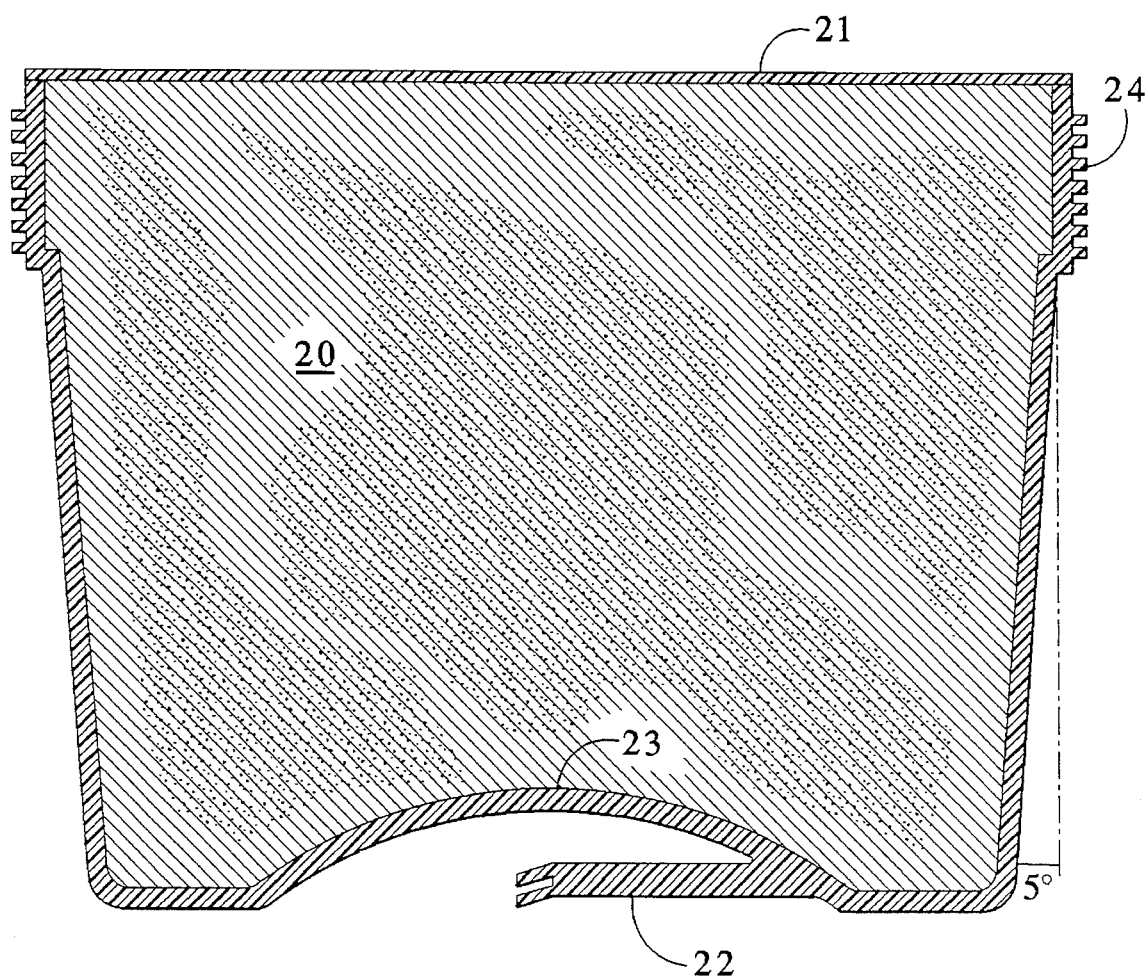
FIG. 3 is a cross-sectional view of a receptacle according to the invention, shown filled to the top with detergent, laundry product, cleaning and rinsing agent, disinfectant and/or preservative and sealed by means of a sheet (e.g., polyvinylalcohol, i.e., PVA, or polyethylene, i.e., PE, retaining sheet) on the open-top end.

The following description illustrates one method of sealing the receptacles according to the invention to prevent flowing-out of filling therefrom when, specifically, the receptacles 20, 30 and 40 are inverted, and placed with the opening facing downwards into the dosing device 80:

a) The receptacles 20, 30 and 40 are filled and sealed with a water insoluble sheet. The sealing is achieved with a polyethylene retaining sheet 21, as shown in FIG. 3, which is later slit open by insertion into the dosing device 80, so that the filling can only flow out when the receptacle is in the dosing device 80;

b) the receptacle 40 is sealed with a water-soluble, sheet 41, which is applied by means of heat-sealing, adhesion or mechanical attachment over the receptacle opening and is supported by the screwed-on lid when the receptacle is being transported. When inserted into a dosing device 80 with the opening facing downwards, and the sheet 41 is sprayed with water, optionally heated water, the sheet 41 dissolves in a short time, so that the powdery or granular contents can then flow onto and through the strainer 81, shown in FIGS. 12 and 13; or c) the receptacle 30 is filled with the detergent or laundry product with or without binder. In the embodiment according to FIG. 4, the receptacle contents are molded by means of a dome-shaped, pressing die, and optionally compacted. In another embodiment not illustrated by a separate drawing, a plane surface can also be produced. A retaining layer consisting of a water-soluble composition is then applied. This composition may comprise a highly viscous, heated melt, a preferably highly viscous, solidifyable solution or a solidifyable powder substance.

Figure 5:
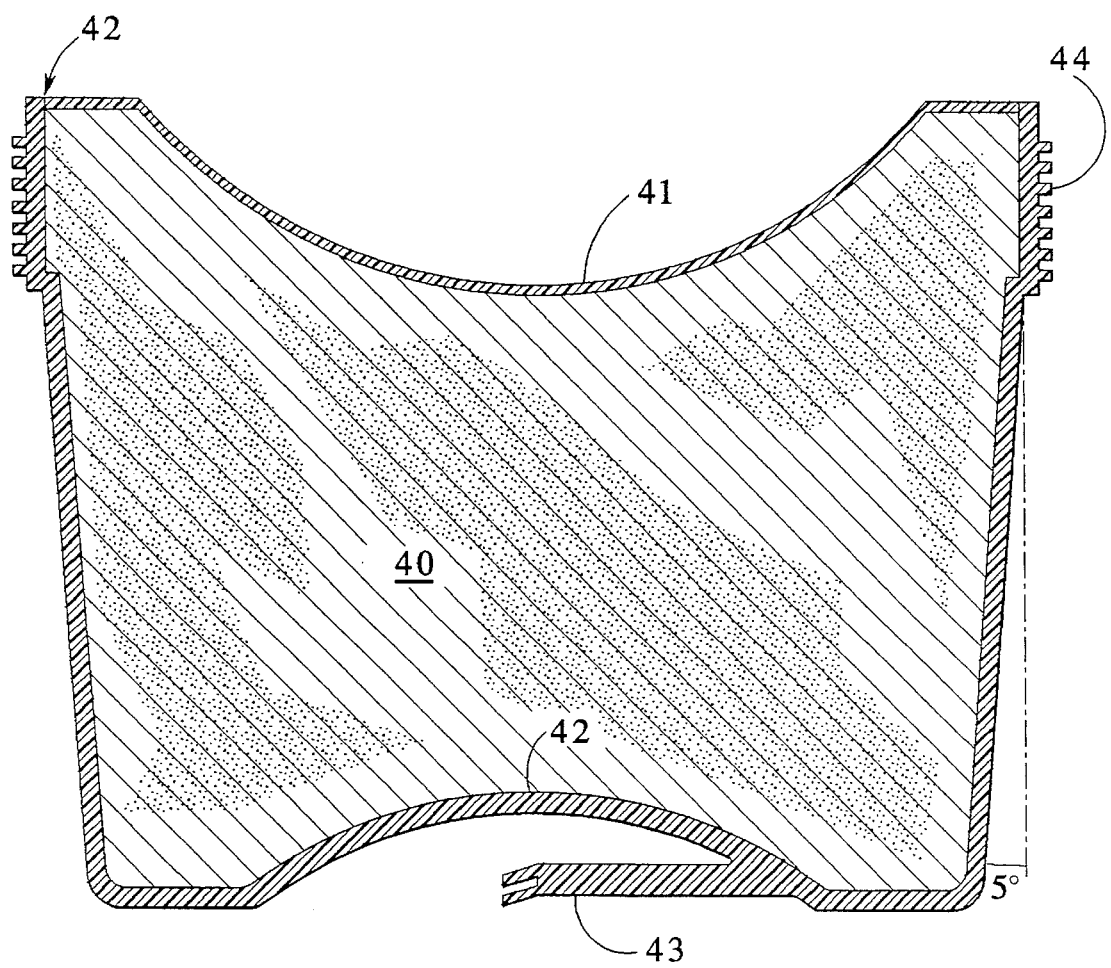
FIG. 5 is a cross-sectional view of a returnable receptacle according to the invention, which has been filled with detergent, laundry agent, cleaning and rinsing agent, disinfectant and/or preservative product (without binder having been added) and onto which a water-soluble PVA molding has been attached and which has then been compacted by means of a dome-shaped press.
Figure 6:
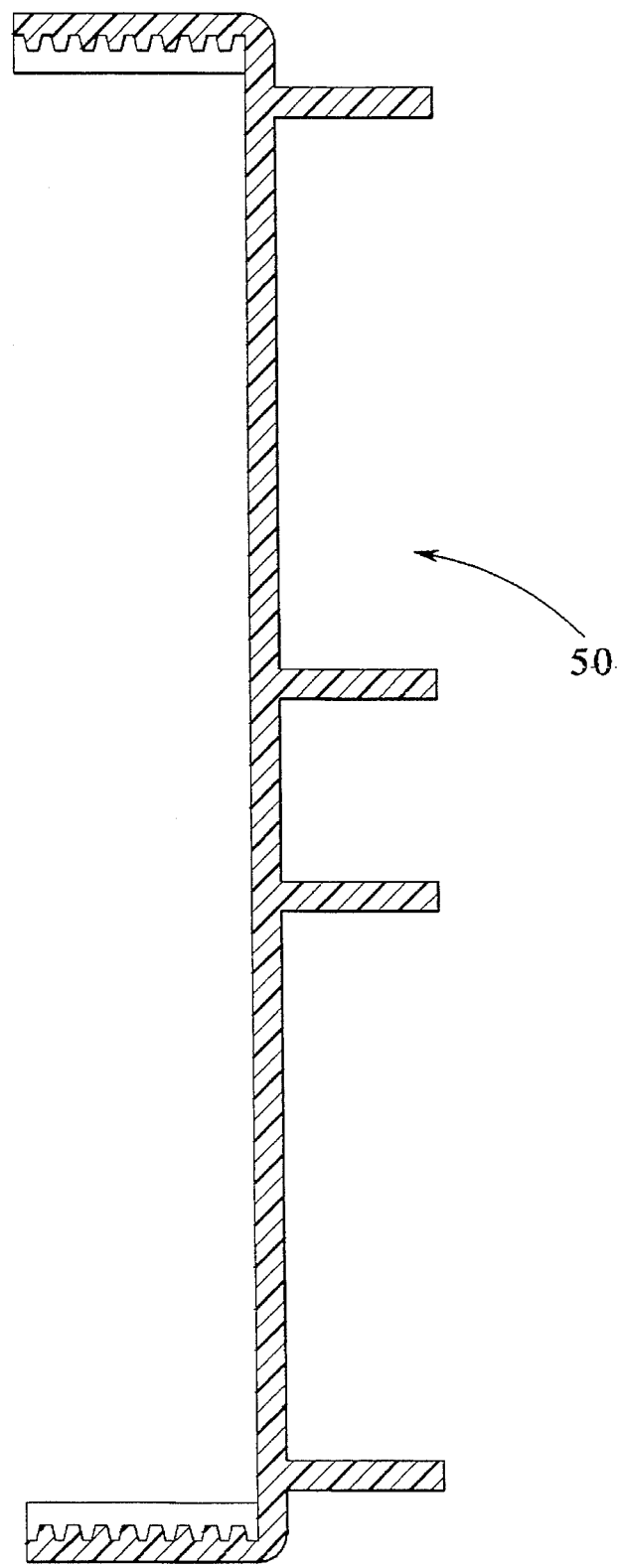
FIG. 6 is a cross-sectional view through a polyethylene cover for a returnable receptacle according to the invention.
Figure 7:
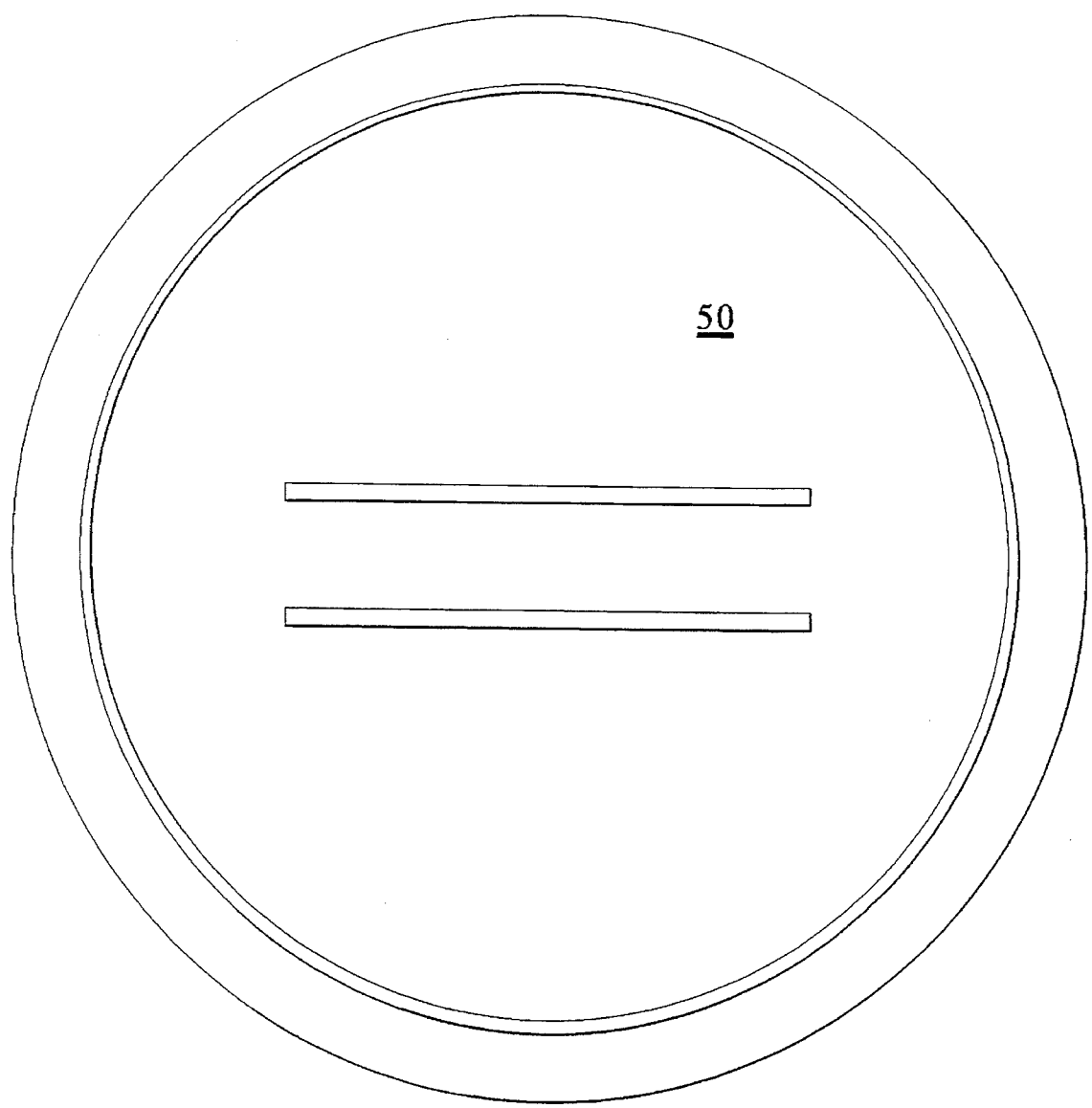
FIG. 7 is a top view of the lid shown in FIG. 6.
Figure 8:
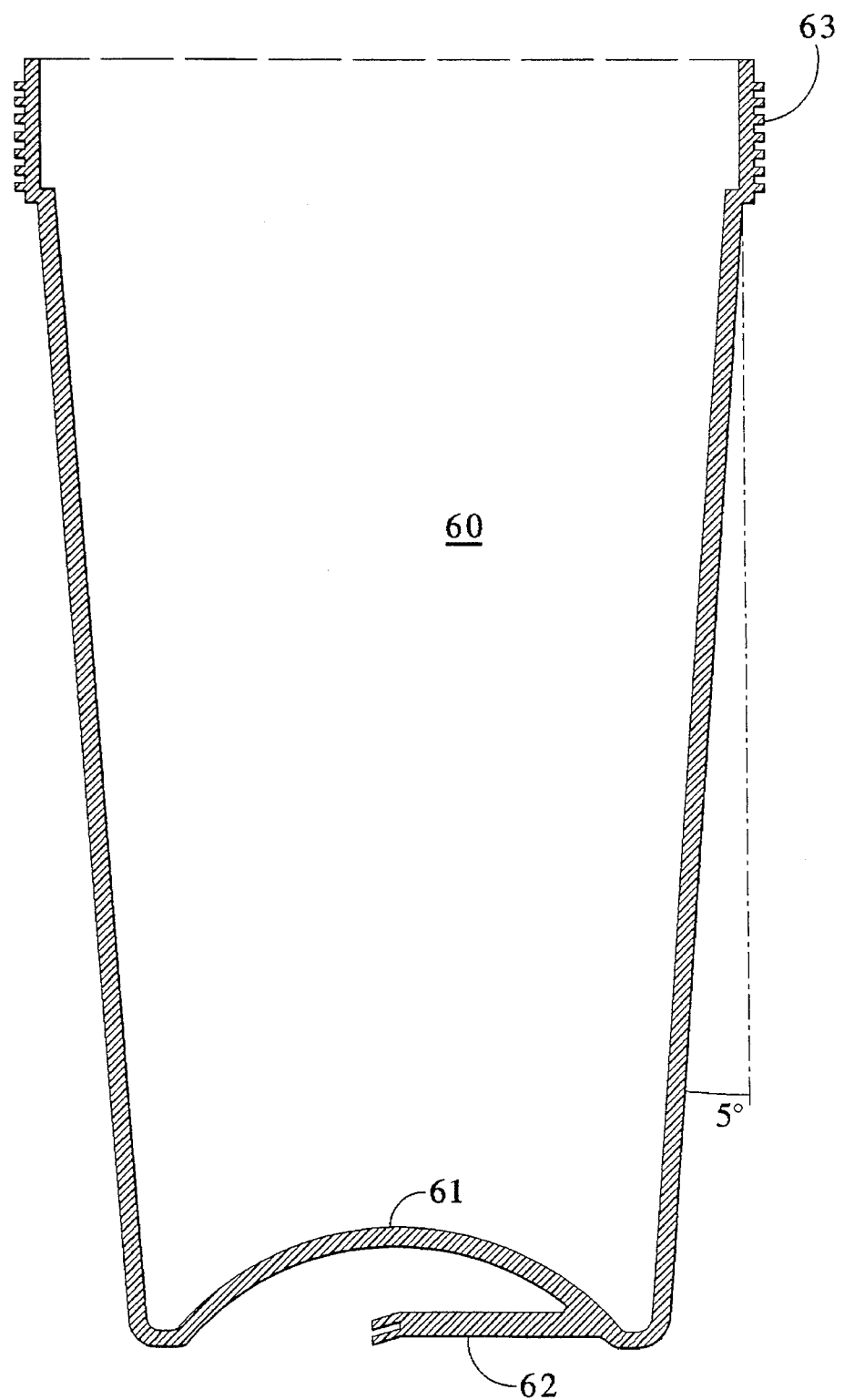
FIG. 8 is a cross-sectional view of a product receptacle according to an alternative embodiment of the invention for use in liquid products and powder granulate material.
Figure 9:
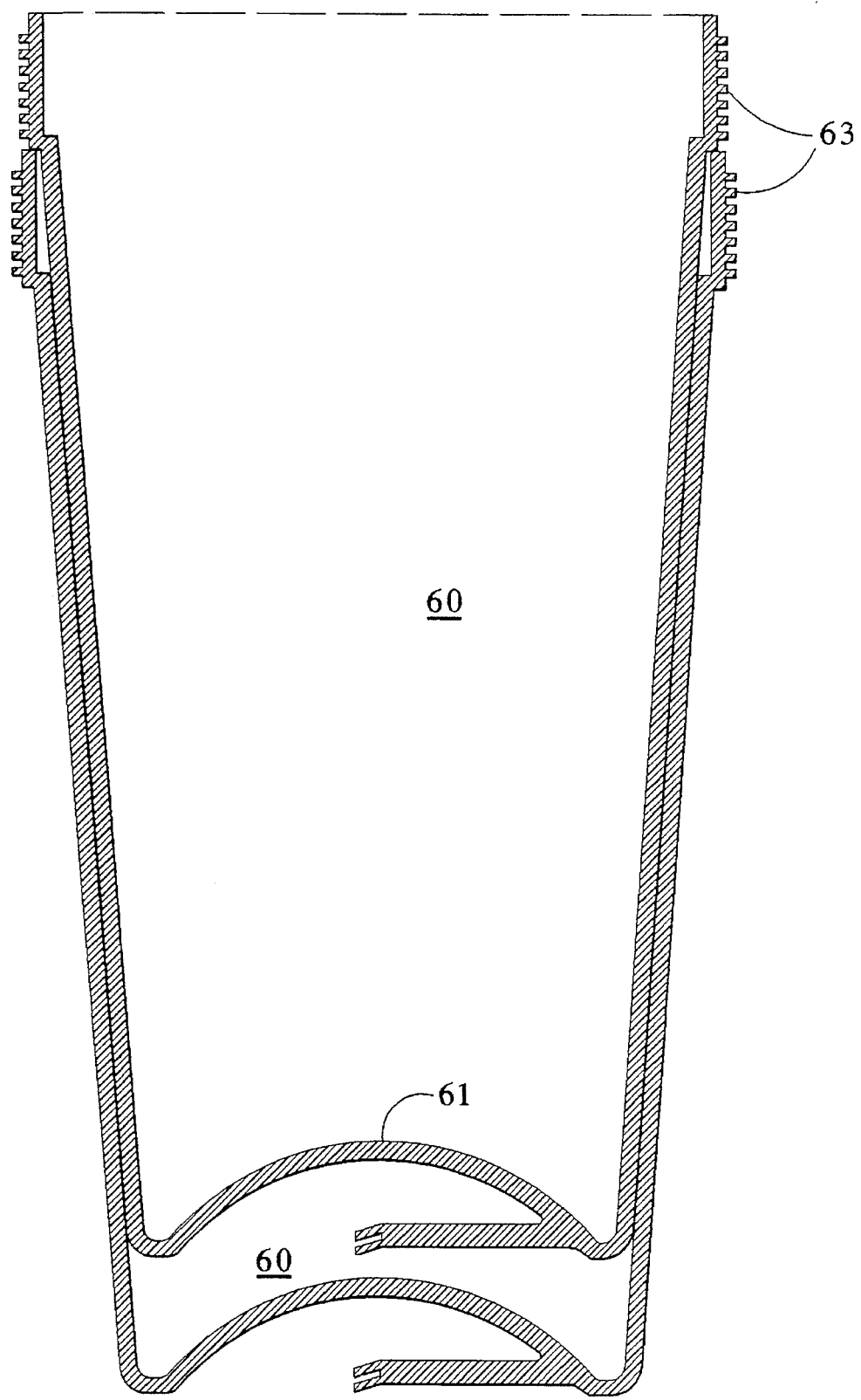
FIG. 9 is a cross-sectional view of two receptacles, as shown in FIG. 8, stacked on each other.

In another embodiment the product is filled with or without binder into the receptacle and a water-soluble, polyvinylalcohol (PVA) layer 41 is applied, followed by subsequent pressing by means of a dome-shaped press. The product receptacle 40 may be provided with additional positive holding or securing points 42 as shown in FIG. 5.

This above-mentioned coating of the powder in the receptacle 20, 30 and 40 with a water-soluble composition, which becomes solid at temperatures between about 0° C. and about 40° C., is effected in such a way that a layer firmly abutting against and adhering to the receptacle wall and having an adequate thickness, e.g., 1 to 2 cm, is formed which prevents the filling from flowing out of the receptacle when the receptacle is turned upside down and being inserted into the dosing device 80. With respect to the chemical composition employed for the layers, the composition thereof must, of course, be compatible with the fillings. Depending on the filling, this may be, e.g., a polyethylene glycol or a derivative thereof of the type having a chemical formula wherein it is terminated by an end group, is solid at temperatures of about 0° C. to 40° C., or may be a crystallizable solution or is a melt, which solidifies at about 0° C. to about 40° C., of one or more salts such as soda, sodium sulfate, alkali polyphosphate or, also an acid, such as citric acid. This "layer-forming" substance is preferably chosen such that upon possible contact with the skin, resulting accidentally when handling the receptacle, this contact does not have any negative consequences such as irritation or burning of the skin. In one case, the sealing layer can be of a composition which is the same as that of the binder in the powder composition. Alternatively, the composition thereof is different from that of the binder.

With respect to the composition employed with the receptacles of the invention, in an especially preferred embodiment of the invention, the composition is achieved by a process which involves mixing a prefabricated premix of powdery and/or granular substances (active substances) with a suitable water-soluble binder, which is liquid at the production temperature, in an amount of between about 1% and about 29%, by weight, based on the weight of the total mixture, so that a "moistened" yet still free-flowing powder composition is obtained. The powder composition obtained is filled into the receptacle and compacted (but not strongly pressed) by applying a pressure, specifically, of about $1 \times 10^4$ to about $1 \times 10^6$ Pa (0.1 to 10 atm), by using a pressure die having the desired surface design, (e.g., plane or dome-shaped). The pressure, while preferred values have been given, need only be sufficient to achieve a level of compaction sufficient to compact the composition into a single integral mass held within the receptacle, i.e., such that detergent is only discharged through dissolution by impingement of a liquid flow thereon. A compact (but not fusion-cast) block results due to subsequent solidification, which still exhibits a powder structure. This block can then by "sealed" with a poured-on solution or melt of a water-soluble substance, so that a sealed, smooth surface is obtained. In contrast to the composition described below, it is not necessary for this sealing layer to have a mechanical strength of its own. Instead it serves to provide a specific appearance, and optionally to protect against skin irritations which may occur when the surface, which may be hazardous to the skin, is contacted.

The described binder may be water, an aqueous solution or a dispersion of one or more water-soluble salts or an organic substance, or a heated flowable melt or a gel. The binder itself may be, but this is not mandatory, crystallizable at temperatures between about 0° C. and about 40° C. The binder is mixed into the composition to achieve moieties having binder in amounts of about 1% to about 29% by weight, preferably 2% to 10% by weight, and especially preferably 3% to 8% by weight, based on the total weight of final mixture.

The binder may, but does not have to, contain components having a cleaning activity. An aqueous solution, 30% to 60% by weight, of alkali-(ortho, pyro or poly)phosphates is especially suitable.

The sealing layer described can be obtained by means of a cast compound having a composition the same as or differing from that of the binder. In contrast to the binder, the cast composition has to be solid or at least gelatinous at temperatures of between about 0° C. and about 40° C. The moiety of the cast composition by weight, based on the total filling, is between about 0% (when then seal is dispensed with, i.e., when there is no sealing layer), and a maximum of about 20%.

The cast composition used for the production of a retaining layer may preferably be of polyethylene glycol or a derivative thereof having a chemical composition terminated by an end group, is solid at about 0° C. to about 40° C., or is a crystallizable solution or melt, solid at about 0° C. to about 40° C., of one or more salts such as soda, sodium sulfate, alkali polyphosphate or is an acid such as citric acid, or is a mixture of these components.

In particular, a mixture consisting of 30% to 50% by weight of water as well as 20% to 50% by weight of sodium polyphosphate, and/or 20% to 50% by weight of soda and/or 20% to 50% by weight of sodium sulfate can be used as the sealing layer. Such a sealing layer contains either only one salt or a combination of two or three suitable salts, and has a solids content between 50% to 70% by weight. In an especially preferred embodiment the sealing layer may consist of a mixture of 50% by weight of water, 25% by weight of sodium polyphosphate and 25% by weight of soda.

The substances usually employed for the detergents, laundry products, cleaning and rinsing agents, disinfectants and preservatives are generally commercially available in powdery or granular form. The individual particles of the active substances of the detergent or laundry product and excipients have preferably a diameter between about 0.01 mm and about 3 mm. The particle size of the components used for the powder mixture is not critical.

In particular, in the case of components available in an industrial quality in usable grain sizes, e.g., about 0.05 mm to about 1.0 mm, such grain sizes will be used directly. The use of powders having a lot of fines, i.e., particles of a size below one or several tenths of a millimeter, is not disadvantageous in the present process.

The blocks produced by the process according to the invention and solidified in the receptacle can be employed for the purpose of washing, cleaning, rinsing as well as disinfecting or for use in antimicrobial treatment, e.g., for the deodorizing treatment of water circulation and water-bearing systems.

The process according to the invention is now explained in more detail by means of the following examples:

EXAMPLE 1 a) powder premixes of the following composition were prepared in a bath mixer (in % by weight each):

|  | A | B | C | D |
|---|---|---|---|---|
| sodium tripolyphosphate | 44 | 29 | 55 | 10 |
| caustic soda beads | 40 | — | 18 | — |
| soda (powder) | 12 | 15 | — | 85 |
| sodium dichloroisocyanurate .2 H$_2$O | 3 | 5 | 2 | — |
| sodium metasilicate (anhydrous) | — | 50 | 25 | — |
| non-ionic surfactant (lutensol ® LF 131) | 1 | 1 | — | 5 | b) a binder mixture made up of 50% of water and 50% of sodium polyphosphate was prepared and brought to a temperature of 20° C.;

c) in each case, 92% by weight of the respective powder mixture A to D was mixed vigorously with an 8% by weight binder mixture. An increase in the temperature was observed during mixing, which subsequently rose to 65° C. to 70° C. The resultant moist but free-flowing powder compositions were filled to the top into the receptacles 20, 30 and 40 of FIGS. 1 to 5, in a volume of 2.5 liters and compacted by means of a minor pressure using a smooth die having a plane surface. The receptacles were then closed with a screw-on lid and stored at room temperature (about 20° C. to 25° C.). Observation after 6 hours showed that a compact mass had formed in the receptacles.

The receptacles could then be inserted with the opening at the top facing downwards into the dosing device 80 on strainer 81 (as shown in FIG. 12), without powdery or granular components flaking off and falling out. The entire receptacle contents can then be removed without any problems by means of a water spray from a nozzle 84 below the strainer 81 as shown in FIG. 12. The emptied receptacles did not contain any visible residue upon completion of the rinsing-out phase.

EXAMPLE 2

The same mixtures as described in items 1a to 1c of Example 1 were prepared in a second test and filled into receptacles. The mixtures were compacted by means of the die. Then 100 ml of a watery mixture comprising 40% by weight of water, 40% by weight of sodium polyphosphate and 20% by weight of soda was heated to 60° C. and was added to each and the respective new mixtures were then automatically spread uniformly on the surface of the mixtures already filled into the receptacles.

The receptacles were screwed tight and allowed to stand at room temperature. After 6 hours of holding time the lids were removed and the compositions were observed. As described under Example 1, a composition resistant to compression had been formed in each case which also showed a uniformly smooth, consistent, solid surface. These receptacles, too, could then be inserted into the dosing device 80 of FIG. 12 with the open top facing downwards, without any problems and rinsed out without leaving any residue by spraying them with water.

EXAMPLE 3

The following powder mixture was prepared in a third test series:

| | |
|---|---|
| sodium hydrogensulfate powder | 60% by weight |
| citric acid monohydrate powder | 10% by weight |
| sodium sulfate (anhydrous) powder | 29.8% by weight |
| non-ionic surfactant (powder) tallow fatty acid alcohol having 25 moles of ethylene oxide) | 0.1% by weight |
| lemon flavor | 0.1% by weight |

This mixture was then treated as explained in steps 1b and 1c of Example 1 in more detail, filled into the receptacles and the powder block was sealed with a composition as described in Example 2 after being compacted by means of the die.

Lids were tightly screwed onto the receptacles and the receptacles with contents therein were allowed to stand at room temperature. After six hours holding time the lids were removed and the filling compositions were observed. As described in Example 1, a compressed composition resulted here as well, which also had a uniformly smooth, consistent, solid surface the receptacles of the invention could also be inserted without any problems with the opening facing downwards into the discharge means 80 of FIG. 12 and rinsed out without any residue by spraying water.

With respect to the recyclable, returnable receptacles of the invention shown in FIGS. 1 through 5, they are open at the top, conically widen upwardly to the open top, and are for use with liquids, solid or powdery detergents, laundry products, cleaning and rinsing agents, disinfectants and/or preservatives, which are especially suitable for carrying out the above-described process according to the invention. The returnable receptacles according to the invention are open and shaped both without stand outs, as mentioned previously (and which throughout this description refers to the fact that the surface of the container has no cuts in the wall with a back taper or recessed from the outer edge of the cut such as to result in a well-like structure capable of trapping residue of substance to be emptied from the container), in the inner wall, and the wall is generally rounded so that all parts can be rinsed out simply and easily (manually and by means of machines). All of the receptacles can be stacked in a space-saving manner. The product receptacles according to the invention are provided with a stacking inclination of about 2° to 7° particularly a stacking inclination of 5° and 3.3°, as more clearly illustrated in FIG. 1, respectively, and are fully open at the filling and dosing opening.

In preferred embodiments the stacking inclination is 3.3° for 5 liter receptacles and 5° for 2.5 liter receptacles.

A stable, external thread 11, for screwing on an also solid screw-on lid, is also located on the open end of the receptacle, on the outside thereof, which lid may be made, e.g., of 2 mm high density, i.e., (HD), polyethylene and a seal. The bottom of the receptacle is provided with a recess and contains a grip projecting into this recess for handling and transporting the receptacle. In one embodiment the recess may be dome-shaped. However, the invention is not restricted to this embodiment.

Both the filled and closed receptacles, and the empty receptacle and the cover, each can be stacked together.

All thermoplastic materials suitable for manufacturing the receptacles and receptacle lids are those producible by means of blow molding or by injection molding. Materials such as polyethylene, polypropylene and particularly, high density polyethylene or polypropylene are preferred. The plastics for the receptacles according to the invention must be chosen such that the receptacles have sufficient dimensional stability, even after occasional impact loads or compressive forces, must be capable of withstanding temperatures of between about 0° C. and about 85° C., and must be able to withstand UV radiation. Furthermore, the plastics for the receptacles have to be compatible with the chemicals with which they are to be filled, particularly detergents, laundry products, cleaning, rinsing and washing agents, disinfectants as well as water-treating agents, even at elevated temperatures of up to about 85° C., as well as being capable of withstanding prolonged exposure times at these temperatures and/or to the chemicals. Thus, returnable, multilayer receptacles can also be used, which are made of an outer or inner polyamide layer and an intermediate barrier layer, for example.

It is desirable that the receptacles according to the invention be reusable, i.e., capable of being refilled. In addition, the production material of the receptacles should be capable of being supplied to what is known as grade-pure recycling, i.e., that it is possible to reproduce the original containers according to the invention with the receptacles being recycled. The costs of packaging in accordance with the invention can then be reduced through the use of the receptacles according to the invention, as compared to presently commercially available receptacles, by factors ranging from 2 to 5.

Upon expiration of the multiple-use period for the receptacles, i.e., due to the wear-and-tear over a predetermined period of time or number of uses, the plastics of the receptacles according to the invention can be recycled (e.g., by plastics granulate recovery) or supplied for unproblematic, thermal utilization, i.e., combustion. For this reason, no plastics such as polyvinylchloride are to be used but only preferably, halogen-free, particularly, chlorine-free plastics are used.

In the case of preferred embodiments of the receptacles according to the invention, an appropriate inscription can be applied to, i.e., burnt onto the exterior of the receptacles by means of, for example, a laser unit.

As shown in FIG. 12, the dosing device 80 includes, for dissolving detergents, laundry products, cleaning and rinsing agents, disinfectants and/or preservatives, a firmly closable receptacle or container having a dosing screen 81 resting upon a base 82, which is intended for receiving and passing therethrough the substances to be dissolved, which are disposed in the product receptacle 20, 30 and 40. A sprayer 84 is arranged concentrically underneath the screen 81 within a receptacle discharge 83, and a discharge nozzle 85 is arranged concentrically in the discharge 83.

The dosing device 80 is filled with the package of the invention as follows. The respective screw-on lids on the respective receptacles 20, 30 and 40 are removed by unscrewing. The rinsing agents or detergents or laundry products contained in the receptacles 20, 30 and 40 at this time cannot flow out due to the applied retaining sheet or retaining layer, or due to the retaining molding, and stay tightly held and protected within the respective receptacle 20, 30 and 40. The product receptacle 20, 30 and 40 is inserted in an appropriately dimensionally shaped dosing device 80, with the open end facing downwards, and placed on a dosing strainer 81, as shown in FIGS. 12 and 13. The dosing strainer 81 may have a number of shapes as will be appreciated by those of ordinary skill in the art. In one embodiment it is dome-shaped. Lid 86 of the dosing device 80 then closes or seals dosing device 80.

When application of a dosage is required, the water-soluble retaining elements (sheet, retaining layer or retaining molding) are initially removed in the dosing device 80 by spraying with an aqueous liquid from sprayer 84. Thereafter, the powder granulate in the receptacles is dissolved by spraying with the aqueous liquid from the sprayer 84. The dosing device 80 can be controlled so as to spray continuously to cause the powder granulate to be dispensed from the product receptacle 20, 30 and 40 until no more cleaning and rinsing agent or detergent or laundry product remains. The control mechanism for the dosing device 80 can include an alarm which gives an alarm (e.g., optically and acoustically) notifying the operator to take out the empty product receptacle and insert an opened, new receptacle filled with the product. Valves and vents, not numbered, as shown in FIG. 13, serve to control the flow of liquid to the dosing device

80. The water flow can be controlled by an electrical control valve in accordance with a predetermined program. A manual valve can be employed to override the electrical control valve in accordance with a predetermined program. A manual valve can be employed to override the electrical control valve to shut off water flow. A gas vent or outflow valve can serve to remove gaseous components from the water line to ensure more accurate measured dosing of detergent by dosing device 80.

Having described the invention, the same will become more readily apparent from the following claims.

What is claimed is:

1. A recyclable, reusable container comprising:

a unitary molded thermoplastic container body including a closed bottom end, an opposed open top end and a sidewall tapering upwardly and outwardly from the bottom end to the top end at a stacking angle of from about 2° to about 7°, an outwardly directed step shoulder defined in the sidewall intermediate the bottom end and the top end of the container body and defining a single outwardly stepped sidewall portion adjacent the top end of the container body and extending between the shoulder and the top end, an outwardly facing surface of the outwardly stepped sidewall portion including an external threaded portion defined thereon for threadably engaging a corresponding set of internal threads provided on a matable cover member, said shoulder being positioned so that when a plurality of the containers are stacked together in a telescoping nested relationship with the bottom end of an upper container being inwardly disposed adjacent the bottom end of an adjacent lower container, the outwardly directed stepped shoulder of the upper container rests against the top end of the adjacent lower container to prevent a vacuum being formed therebetween to facilitate unstacking of the containers for use and so that only the externally threaded stepped sidewall portion of the upper container remains exposed above and adjacent the externally threaded stepped sidewall portion of the lower container to provide minimum stack height, the bottom end including an inwardly and upwardly directed dome-shaped region therein including a handle grip portion defined in an outwardly facing side of the dome-shaped region, the container body defining an open, smoothly rounded container cavity without any undercut portions adapted to storably receive and completely discharge material contents placed therein for storage and dispensing.

2. A container as defined in claim 1 further comprising a cover member for selectively closing the open end of the container body including a body portion having a depending peripheral flange with an internal threaded portion defined on an inwardly facing surface of the flange, said cover member being releasably threaded by engaged on said open top end of the container body with the internal threaded portion of the cover member engaged with the external threaded portion of the stepped sidewall portion of the container body.

3. A container as defined in claim 2, further including a degassing valve defined in said cover member.

4. A container as defined in claim 2, further including a reclosable opening defined in the cover member.

5. A container as defined in claim 2, wherein said cover member includes outwardly facing means for receiving a bottom end of a container body to provide a stable support for a plurality of closed containers stacked one on top of another.

6. A container as defined in claim 2, wherein the cover member includes a recessed handle member defined on an outwardly facing side thereof.

7. A container as defined in claim 1, wherein said container body is molded from a high grade, dimensionally stable, UV-resistant and chemical resistant thermoplastic molding resin selected from polyolefin resins.

8. A container as defined in claim 2, further comprising a seal disposed in said cover member for sealing the open top end of the container body when the cover member is threadedly engaged on said container body.

\* \* \* \* \*